United States Patent [19]

Kawamura et al.

[11] Patent Number: 4,910,201

[45] Date of Patent: Mar. 20, 1990

[54] 3(2H)-PYRIDAZINONE DERIVATIVES, AND THEIR USES IN INSECTICIDAL COMPOSITIONS

[75] Inventors: Yasuo Kawamura; Tomoyuki Ogura; Yasuo Kawamura, both of Funabashi; Masayoshi Hirose, Minamisaitama; Kiminori Hirata, Minamisaitama; Masaki Kudo, Minamisaitama; Toshiro Miyake, Minamisaitama, all of Japan

[73] Assignee: Nissan Chemical Industries, Ltd., Tokyo, Japan

[21] Appl. No.: 75,725

[22] Filed: Jul. 20, 1987

Related U.S. Application Data

[63] Continuation-in-part of Ser. No. 889,255, Jul. 25, 1986.

[30] Foreign Application Priority Data

Jul. 30, 1985 [JP] Japan ................................. 60-168229
Jun. 27, 1986 [JP] Japan ................................. 61-152364

[51] Int. Cl.$^4$ .................... C07D 237/06; A61K 31/50
[52] U.S. Cl. .................................. 514/247; 514/252; 544/238; 544/239; 544/240; 544/241
[58] Field of Search ............... 544/238, 239, 240, 241; 514/252, 247

[56] References Cited

U.S. PATENT DOCUMENTS 4,571,397 2/1986 Taniguchi et al. .................. 514/252
4,663,324 5/1987 Graf et al. ............................ 514/247

FOREIGN PATENT DOCUMENTS 0088384 9/1983 European Pat. Off. .
429344 5/1942 Japan .
5859973 2/1981 Japan .
5859974 2/1981 Japan .
917849 2/1963 United Kingdom .

Primary Examiner—Nicholas S. Rizzo
Attorney, Agent, or Firm—Oliff & Berridge

[57] ABSTRACT

Novel 3(2H)-pyridazinone derivatives of the formula (I):

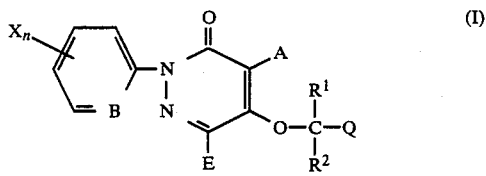

wherein,
X represents a halogen, an alkyl, a haloalkyl, a haloalkoxy atoms, NO$_2$, an alkoxy or

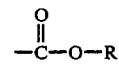

(wherein, R represents an alkyl);
n is 1 to 4;
A represents hydrogen, a halogen, an alkyl or an alkoxy;
B represents CX$_1$ (wherein, X$_1$ represents H or a halogen) or N;
R$^1$ and R$^2$ represent each independently H or an alkyl;
E represents H, a halogen, an alkoxy or —OH; and
Q represents:

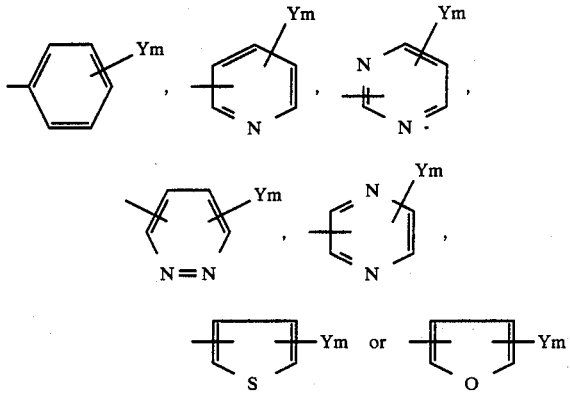

(wherein, Y represents a halogen, an alkyl, an alkoxy, a haloalkyl, a haloalkoxy, CN,

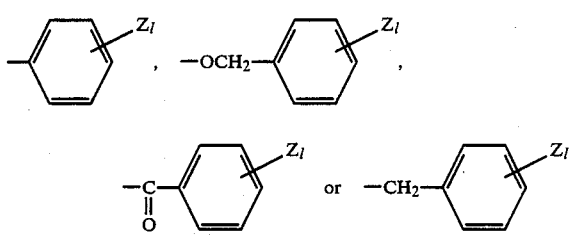

(wherein, Z represents a halogen, an alkyl, an alkoxy or a haloalkyl atoms, and l is 0, 1 to 5, said Z being the same or different when l is 2 to 5); and m is 1 to 5, said Y being the same or different when n is 2 to 4. A process for preparation of said derivatives is also provided. These derivatives are useful as an active ingredient of insecticidal composition.

7 Claims, No Drawings

3(2H)-PYRIDAZINONE DERIVATIVES, AND THEIR USES IN INSECTICIDAL COMPOSITIONS

This is a continuation-in-part of U.S. patent application Ser. No. 889,255, filed July 25, 1986.

BACKGROUND OF THE INVENTION

This invention relates to novel 3(2H)-pyridazinone derivatives, process for preparation thereof, and insecticidal compositions containing said derivatives as an active ingredient.

The present inventors have previously found that a part of the compounds of the general formula (IV) below has insecticidal, acaricidal, nematicidal, fungicidal activities for agricultural and horticultural uses (refer to European Laid-open Patent Publication No. 0,088,384):

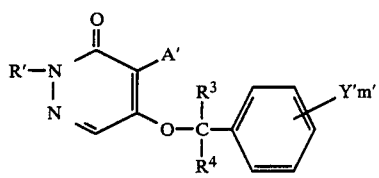

wherein R' represents, for example, an alkyl; A' represents a halogen; and $R^3$ and $R^4$ represent hydrogen or a lower alkyl.

One of the main features of these known compounds resides in that R' is an alkyl. On the other hand, British Pat. No. 917,849 Publication discloses 3(2H)-pyridazinone derivatives of the formula (V):

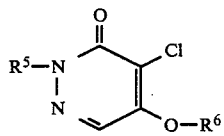

This publication also discloses that the known compound A below is included in the compounds of the formula (V).

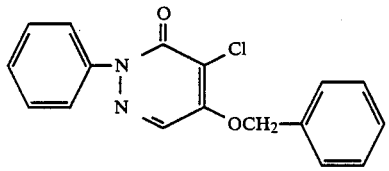

However, both the two phenyl rings in the compound A are unsubstituted. Moreover, there is no description in this publication as to the use for an insecticide that is intended in the present invention although the publication disclosed that the compounds A are used for agricultural drugs which affect the growth of plants.

In addition, Japanese Patent Publication No. 09344/67 discloses 3(2H)-pyridazinone derivatives of the formula (VI):

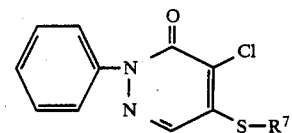

wherein $R^7$ represents, for example, benzyl or 4-chlorobenzyl.

One of the main features of these known compounds (VI), however, resides in that the compounds have a thioether group. Moreover, there is not described such compounds wherein both the two phenyl rings are substituted. The physiological activities described therein are restricted to fungicidal activity and central nerve-depressive activity. Thus, the compounds (VI) are apparently different from the compounds according to the present invention.

SUMMARY OF THE INVENTION

An object of the present invention is to provide novel 3(2H)-pyridazinone derivatives.

Another object of the invention is to provide a process for preparing such novel 3(2H)-pyridazinone derivatives.

Still another object of the invention is to provide insecticidal compositions containing such novel 3(2H)-pyridazinone derivatives as an active ingredient.

Still further object of the invention is to provide a method for insecticidal treatment in the agricultural and horticultural field with the effective amount of a compound of the formula (I).

DETAILED DESCRIPTION OF THE INVENTION

The novel 3(2H)-pyridazinone derivatives according to the present invention are represented by the general formula (I):

wherein

X represents a halogen, an alkyl having 1 to 6 carbon atoms, a haloalkyl having 1 to 4 carbon atoms, a haloalkoxy having 1 to 4 carbon atoms, nitro, an alkoxy having 1 to 4 carbon atoms or

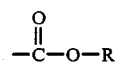

(wherein R represents an alkyl having 1 to 4 carbon atoms);

n is an integer of from 1 to 4;

A represents a halogen, an alkyl having 1 to 4 carbon atoms, an alkoxy having 1 to 4 carbon atoms or hydrogen;

B represents $CX_1$ (wherein $X_1$ represents hydrogen or a halogen) or nitrogen;

$R^1$ and $R^2$ represents each independently hydrogen or an alkyl having 1 to 4 carbon atoms;

E represents hydrogen, a halogen, an alkoxy having 1 to 4 carbon atoms or hydroxyl; and Q represents

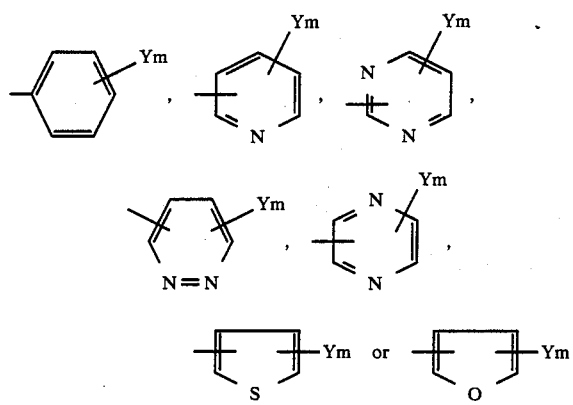

(wherein Y represents a halogen, an alkyl having 1 to 6 carbon atoms, an alkoxy having 1 to 6 carbon atoms, a haloalkyl having 1 to 4 carbon atoms, a haloalkoxy having 1 to 4 carbon atoms, cyano,

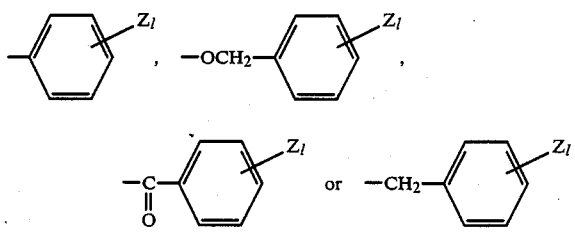

(wherein Z represents a halogen, an alkyl having 1 to 4 carbon atoms, an alkoxy having 1 to 4 carbon atoms or a haloalkyl having 1 to 4 carbon atoms; and is 0 or an integer of from 1 to 5, said Z being the same or different when is an integer of from 2 to 5); and m is an integer of from 1 to 5, said Y being the same or different when m is an integer of from 2 to 5), said X being the same different when n is an integer of from 2 to 4.

The present inventors have conducted intensive researches on insecticidal activity of the novel 3(2H)-pyridazinone derivatives of the formula (I) described above and have found that the compounds of the invention have excellent and effective activities for the control of insect pests to accomplish the present invention.

The compounds of the invention are quite different from conventional insecticides in that they exhibit extremely strong and specific action against a certain kind of insect pests and also have excellent residual action to exhibit highly effective control of insect pests.

Namely, the compounds according to the invention strongly disturb physiological process of transformation (metamorphosis) and casting off (ecdysis) of insect pests caused by insect hormone to malform the insect pests and inhibit casting off thereof, being totally different from conventional drugs which act on the nervous systems of insect pests, such as organic chlorine-insecticides, organic phosphorus-insecticide, carbamate-insecticides and pyrethroide insecticides of the prior art. Such inhibition of casting off causes some pests to die and thus, together with the excellent residual action of the present compounds, the compounds of the invention exhibit highly effective control of insect pests.

Such selective control, unlike prior art methods, is very useful for protecting cultivated crops without destroying an ecosystem, because of very small effects on natural enemies against insect pests including predatory mites (e.g., *Amblyseius longispinosus*) and also on useful insects. Moreover, the compounds of the invention are excellent in safety because of low toxicity to warm-blooded animals and fish.

Among the compounds of the present invention, following compounds are preferable in respect to insecticidal activities.

Compounds of the general formula (IA):

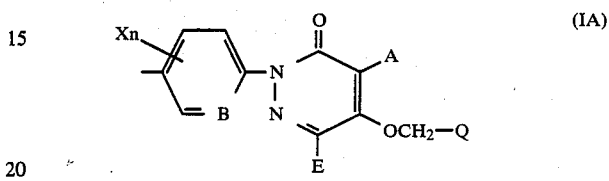

wherein E represents hydrogen, chlorine or methoxy; A represents hydrogen, chlorine, bromine, fluorine, iodine or methyl; B represents nitrogen or $CX_1$ (wherein $X_1$ represents hydrogen or a halogen); X represents a halogen, and alkyl having 1 to 4 carbon atoms, and alkoxy having 1 to 4 carbon atoms, $NO_2$, $CO_2R$ (wherein R represents an alkyl having 1 to 4 carbon atoms) or a haloalkoxy having 1 to 4 carbon atoms; n is an integer of from 1 to 4; Q represents:

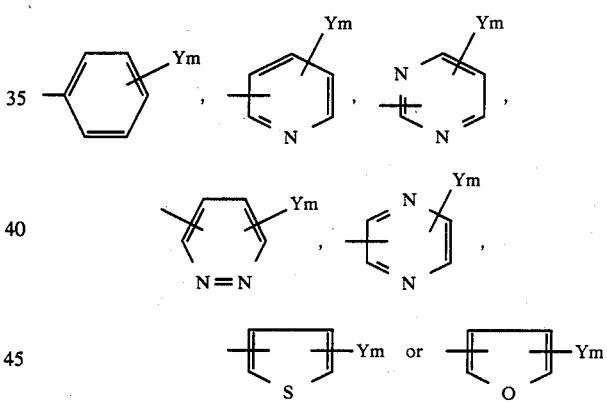

Y represents a halogen, an alkyl having 1 to 4 carbon atoms, a haloalkyl having 1 to 3 carbon atoms, haloalkoxy having 1 to 3 carbon atoms or an alkoxy having 1 to 4 carbon atoms; and m is an integer of from 1 to 5, said X being the same or different when n is an integer of from 2 to 4 and said Y being the same or different when m is an integer of from 2 to 5.

More preferred are those represented by the Formula (IB):

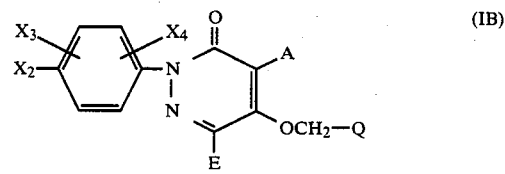

wherein E represents hydrogen; A represents hydrogen, chlorine, bromine, fluorine or iodine; $X_2$ represents a halogen, hydrogen or nitro; $X_3$ and $X_4$ represents each independently hydrogen, a halogen, nitro or an alkyl having 1 to 3 carbon atoms; Q represents:

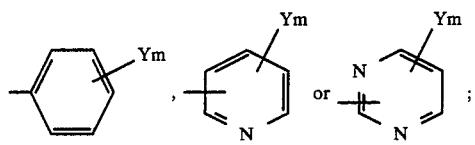

Y represents a halogen or a haloalkyl having 1 to 3 carbon atoms; and m is an integer of 1 or 2, and Y being the same or different when m is 2.

Particularly preferred are the compounds of the formula (IC):

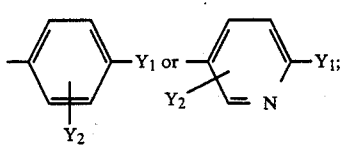
(IC)

wherein E represents hydrogen; A represents chlorine, bromine, fluorine or iodine; $X_5$ represents hydrogen, halogen or nitro; $X_6$ represents hydrogen, nitro or halogen; Q represents

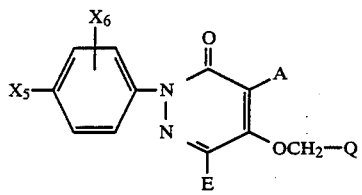

$Y_1$ represents a halogen; and $Y_2$ represents hydrogen or a halogen.

More specifically, among the compounds listed in Table 1-a and 1-b given later, preferable compounds are shown in Table 6. Among them, the most preferable compounds are Nos. 340, 341, 393, 507, 508, 582, 583, 607 and 608.

The compounds of the invention can be produced according to the following reaction:

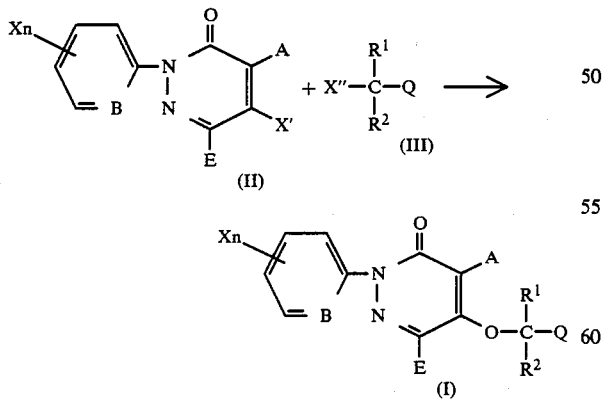

wherein $R^1$, $R^2$, A, B, E, X, Q and n are defined above, and X' and X" represent a halogen or —OM (wherein M represents hydrogen or an alkali metal), provided that X" represents a halogen when X' is —OM and X" represents —OM when X' is a halogen.

More specifically, the compounds of the invention can be prepared according to the following Reaction (1) or (2).

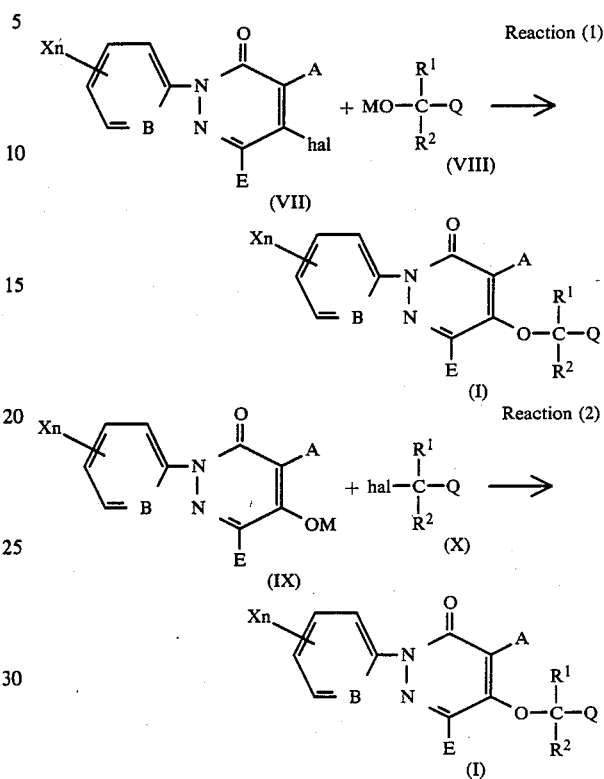

In the Reaction (1) and (2), $R^1$, $R^2$, A, B, E, X, Q, M and n are as defined above and hal represents a halogen.

The compounds of the invention can be produced by reacting one of the starting materials, a 3(2H)-pyridazinone derivative of the formula (VII) or (IX) above, with another starting compound of the formula (VIII) or (X) above in an appropriate solvent in the presence of a hydrogen halide-absorbing agent. It should be noted, however, that the hydrogen halide-absorbing agent is not always required when M represents an alkali metal.

As the solvent can be used lower alcohols such as methanol, and ethanol; ketones such as acetone and methylethyl ketone; hydrocarbons such as benzene and toluene, ethers such as isopropyl ether, tetrahydrofuran and 1,4-dioxane; amides such as N,N-dimethyl-formamide and hexamethyl phosphoric triamides; and halogenated hydrocarbons such as dichloromethane and dichloroethane. As necessary, these solvents can be used as a mixture with water.

As the hydrogen halide-absorbing agent can be used inorganic bases such as sodium hydride, sodium hydroxide, potassium hydroxide, sodium carbonate, potassium carbonate and sodium bicarbonate; and organic bases such as sodium methoxide, sodium ethoxide, triethylamine and pyridine. As necessary, there may be added to the reactive system a catalyst such as tetraammonium salts (e.g., triethylbenzylammonium chloride).

The reaction temperature ranges from −20° C. to the boiling point of the solvent to be used in the reaction. However, the reaction temperature in the range of from −5° C. to the boiling point of the solvent used is desirable.

The molar ratio of the starting materials can be optionally selected. However, it is advantageous to conduct the reaction using equimolar or nearly equimolar amount of the materials.

Incidentally, the compounds of the formula (IX) above can be prepared by a process according to the following reaction:

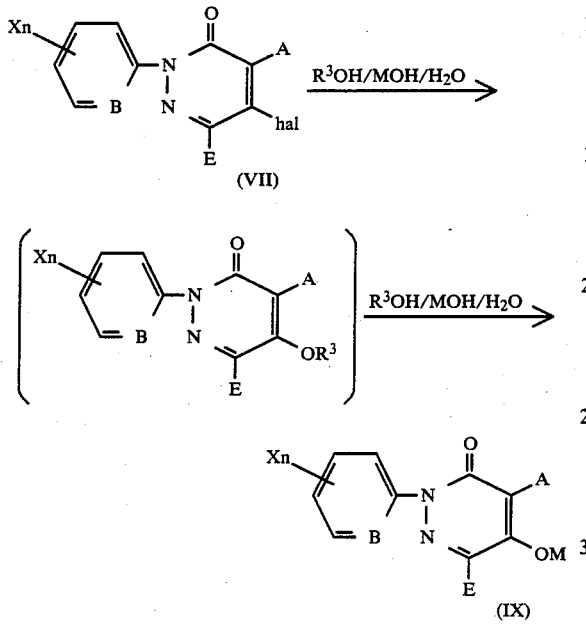

wherein X, A, B, E, M, n and hal are as defined in the above and $R^3$ represents methyl or ethyl.

The compounds encompassed by the present invention are illustrated by the compounds listed in Tables 1-a and 1-b below. However, it should be understood that the compounds in Tables 1-a and 1-b are merely illustrated and not to restrict the invention.

Incidentally, a compound of the invention which contains asymmetric carbon atom(s) includes optically active (+) compound and (−) compound.

Preparations of the compounds (I) of the invention as well as the compounds of the formula (IX) to be used as one of the starting materials are described in detail by way of the following examples which are not to restrict the invention.

REFERENCE EXAMPLE 1

Synthesis of 4-chloro-5-hydroxy-2-(4-chlorophenyl)-3(2H)-pyridazinone

In 140 ml of water was dissolved 18.3 g (0.28 mol) of potassium hydroxide, and thereto were added 25.6 g (0.093 mol) of 4,5-dichloro-2-(4-chlorophenyl)-3(2H)-pyridazinone and 140 ml of ethanol. The reaction mixture was refluxed for 6 hours. After allowing to cool, ethanol was distilled off from the mixture under reduced pressure and then 300 of water was added to the mixture. Insoluble matter was removed by filtration and filtrate was acidified with hydrochloric acid. The solid thus precipitated was taken out by filtration, washed with water, and recrystallized from ethanol to give 11.1 g of the intended compound having melting point (hereinafter referred to as "m.p.") of 270°–271° C.

SYNTHESIS EXAMPLE 1

Synthesis of 4-chloro-5-(4-chlorobenzyloxy)-2-(4-chlorophenyl)-3(2H)-pyridazinone (Compound No. 27)

In 70 ml of N,N-dimethylformamide was dissolved 7.1 g (0.028 mol) of 4-chloro-2-(4-chlorophenyl)-5-hydroxy-3(2H)-pyridazinone, and thereto were added 4.5 g of p-chlorobenzyl chloride and 5.4 g of anhydrous potassium carbonate. The resulting reaction mixture was heated under stirring on an oil bath at 120° to 130° C. for 2 hours. After allowing to cool, the reaction mixture was poured into 500 ml of water. The solid thus precipitated was taken out by filtration, washed with water, dried and then recrystallized from an ethyl acetate-benzene mixture to give 6.3 g of the intended compound.

m.p. 184.5°–186.0° C.

$^1$H-NMR (CDCl$_3$, δ, TMS); 5.39 (2H, s), 7.30–7.69 (8H, m), 8.00 (1H, s).

SYNTHESIS EXAMPLE 2

Synthesis of 4-bromo-5-(4-chlorobenzyloxy)-2-(4-chlorophenyl)-3(2H)-pyridazinone (Compound No. 28)

In 35 ml of N,N-dimethylformamide were dissolved 1.5 g (4.1 m mol) of 2-(4-chlorophenyl)-4,5-dibromo-3(2H)-pyridazinone and 0.59 g (4.1 m mol) of p-chlorobenzyl alcohol, and thereto was added 0.27 g of powdery potassium hydroxide. The reaction mixture was stirred for one day at room temperature. The resulting solution was poured into water and extracted with ethyl acetate. The extract was washed with water, dried over anhydrous sodium sulfate and freed of solvent by distillation under reduced pressure. The crystals thus obtained were recrystallized from ethyl acetate-benzene to give 1.4 g of the intended compound.

m.p. 168.5°–175.1° C.

$^1$H-NMR (CDCl$_3$, δ, TMS); 5.29 (1H, s), 7.30–7.65 (8H, m), 7.74 (1H, s).

SYNTHESIS EXAMPLE 3

Synthesis of 4-chloro-5-(4-chloro-α-methylbenzyloxy)-2-(4-chlorophenyl)-3(2H)-pyridazinone (Compound No. 29)

In 30 ml of N,N-dimethylformamide were dissolved 1.0 g (3.6 m mol) of 2-(4-chlorophenyl)-4,5-dichloro-3(2H)-pyridazinone and 0.57 g (3.6 m mol) of p-chloro-α-methylbenzyl alcohol, and thereto was added 0.24 g of powdery potassium hydroxide. The reaction mixture was stirred at room temperature for 2 days.

The resulting solution was poured into water and extracted with ethyl acetate. The extract was washed with water, dried over anhydrous sodium sulfate and freed of ethyl acetate by distillation under reduced pressure. The oil thus obtained was purified by means of column chromatography (on silica gel, eluting with benzene/ethyl acetate=15/1) and recrystallization (from benzene/n-hexane) to give 300 mg of the intended compound.

m.p. 135.0°–138.0° C.

$^1$H-NMR (CDCl$_3$, δ, TMS); 1.72 (3H, d, J=6.2 Hz), 5.55 (1H, q, J=6.2 Hz), 7.19–7.62 (8H, m), 7.66 (1H, s).

SYNTHESIS EXAMPLE 4

Synthesis of 4-chloro-2-(4-chlorophenyl)-5-(4-trifluoromethylbenzyloxy)-3(2H)-pyridazinone (Compound No. 49)

In 30 ml of N,N-dimethylformamide were dissolved 1.0 g (3.6 m mol) of 2-(4-chlorophenyl)-4,5-dichloro-3(2H)-pyridazinone and 0.64 g (3.6 m mol) of p-trifluoromethylbenzyl alcohol, and thereto was added 0.24 g of powdery potassium hydroxide. The reaction mixture was stirred at room temperature for one day. Then, the procedures in Synthesis Example 2 were repeated to give 900 mg of the intended compound.

m.p. 186.0°–188.0° C.

$^1$H-NMR (CDCl$_3$, δ, TMS); 5.37 (2H, s), 7.21–7.81 (8H, m), 7.88 (1H, s).

SYNTHESIS EXAMPLE 5

Synthesis of 4-chloro-5-(4-chlorobenzyloxy)-2-(4-trifluoromethylphenyl)-3(2H)-pyridazinone (Compound No. 109)

In 50 ml of N,N-dimethylformamide were dissolved 2.0 g (6.5 m mol) of 4,5-dichloro-2-(4-trifluoromethylphenyl)-3(2H)-pyridazinone and 0.92 g (6.5 m mol) of p-chlorobenzyl alcohol, and thereto was added 0.51 g of powdery potassium hydroxide. Then, the procedures in Synthesis Example 2 were repeated to give 1.94 g of the intended compound.

m.p. 171.0°–175.0° C.

$^1$H-NMR (CDCl$_3$, δ, TMS); 5.35 (2H, s), 7.37 (4H, s), 7.71 (4H, s), 7.89 (1H, s).

mass spectrum m/e; 414 (M+), 125.

SYNTHESIS EXAMPLE 6

Synthesis of 4-chloro-5-(4-chlorobenzyloxy)-2-(2,4-difluorophenyl)-3(2H)-pyridazinone (Compound No. 154)

In 20 ml of N,N-dimethylformamide was dissolved 1.03 g (7.2 m mol) of p-chlorobenzyl alcohol, and thereto was added 0.31 g of 55% sodium hydride. The reaction mixture was stirred at room temperature for 30 minutes. To the resulting solution was added dropwise a solution of 2.0 g of 4,5-dichloro-2-(2,4-difluorophenyl)-3(2H)-pyridazinone in 50 ml of N,N-dimethylformamide. After stirring the resulting mixture for one day at room temperature, the procedures in Synthesis Example 1 were repeated to give 1.5 g of the intended product.

m.p. 166.6°–166.9° C.

$^1$H-NMR (CDCl$_3$, δ, TMS); 5.31 (2H, s), 6.28–7.57 (7H, m), 7.86 (1H, s).

SYNTHESIS EXAMPLE 7

Synthesis of 4-chloro-5-(4-chlorobenzyloxy)-2-(4-chloro-2-fluorophenyl)-3(2H)-pyridazinone (Compound No. 170)

In 30 m, of N,N-dimethylformamide were dissolved 1.0 g (3.4 m mol) of 2-(4-chloro-2-fluorophenyl)-4,5-dichloro-3(2H)-pyridazinone and 0.48 g (3.4 m mol) of p-chlorobenzyl alcohol, and thereto was added 0.22 g of powdery potassium hydroxide. Then, the procedures in Synthesis Example 2 were repeated to give 920 mg of the intended compound.

m.p. 167.3°–167.9° C.

$^1$H-NMR (CDCl$_3$, δ, TMS); 5.33 (2H, s), 7.20–7.40 (7H, m), 7.85 (1H, s).

SYNTHESIS EXAMPLE 8

Synthesis of 2-(5-chloropyridine-2-yl)-4-chloro-5-(4-chlorobenzyloxy)-3(2H)-pyridazinone (Compound No. 235)

In 30 ml of N,N-dimethylformamide were dissolved 1.5 g (5.1 m mol) of 2-(5-chloropyridine-2-yl)-4,5-dichloropyridazinone and 0.73 g (5.1 m mol) of p-chlorobenzyl alcohol, and thereto was added 0.34 g of powdery potassium hydroxide. Then, the procedures in Synthesis Example 2 were repeated to give 500 mg of the intended compound.

m.p. 166.7°–169.0° C.

$^1$H-NMR (CDCl$_3$, δ, TMS); 5.34 (2H, s), 7.35 (4H, s), 7.67–7.84 (2H, m), 7.93 (1H, s), 8.53 (1H, d, J=2 Hz).

SYNTHESIS EXAMPLE 9

Synthesis of the compound obtained in Synthesis Example 7 (Compound No. 170) by another procedure In 50 ml of N,N-dimethylformamide was dissolved 2.75 g (0.01 m mol) of 4-chloro-2-(4-chloro-2-fluorophenyl)-5-hydroxy-3(2H)-pyridazinone, and thereto was added 0.44 g of 55% sodium hydride. The mixture was stirred at room temperature for 10 minutes. The resulting solution was incorporated with 1.6 g of p-chlorobenzyl chloride and then stirred at 100° to 110° C. for 2 hours. Then, the procedures in Synthesis Example 1 were repeated to give 2.1 g of the intended product.

SYNTHESIS EXAMPLE 10

Synthesis of 4-bromo-5-(4-chloro-2-fluorobenzyloxy)-2-(3,4-dichlorophenyl)-3(2H)-pyridazinone (Compound No. 522)

To a mixture of 2.0 g (5.0 m mol) of 4,5-dibromo-2-(3,4-dichlorophenyl)-3(2H)-pyridazinone and 0.84 g (5.2 m mol) of 4-chloro-2-fluorobenzyl alcohol was added 80 ml of N,N-dimethylformamide. The resulting mixture was cooled with ice, incorporated with 0.4 g of potassium hydroxide and then stirred for one day. Then, the procedures in Synthesis Example 2 were repeated to give a crude product. The crude product was recrystallized from benzene to give 1.3 g of the intended compound.

m.p. 172.0°–173.0° C.

$^1$H-NMR (CDCl$_3$, δ, TMS); 5.57 (2H, s), 7.25–7.95 (6H, m), 8.43 (1H, s).

SYNTHESIS EXAMPLE 11

Synthesis of 4-chloro-2-(4-chlorophenyl)-5-{(6-chloro-3-pyridyl)methyloxy}-3(2H)-pyridazinone (Compound No. 340)

The procedures in Synthesis Example 2 were repeated by using 2.0 g (7.2 m mol) of 2-(4-chlorophenyl)-4,5-dichloro-3(2H)-pyridazinone, 1.1 g (7.7 m mol) of 6-chloro-3-pyridine methanol, 0.4 g of potassium hydroxide and 80 ml of N,N-dimethylformamide to give 1.7 g of the intended product (recrystallized from benzene/n-hexane).

m.p. 190.0°–192.0° C.

$^1$H-NMR (CDCl$_3$, δ, TSM); 5.51 (2H, s), 7.22–7.71 (5H, m), 7.90 (1H, dd, J=2 Hz 8 Hz), 8.34 (1H, s), 8.50 (1H, d, J=2 Hz).

SYNTHESIS EXAMPLE 12

Synthesis of 4-chloro-2-(4-chlorophenyl)-5-{(5-methyl-2-thienyl)-methoxyloxy}-3(2H)-pyridazinone, (Compound No. 323)

The procedures in Synthesis Example 11 were repeated by using 2.0 g (7.3 m mol) of 2-(4-chlorophenyl)-4,5-dichloro-3(2H)-pyridazinone, 1.0 g (7.8 m mol) of 5-methyl-2-thiophene methanol, 0.4 g of potassium hydroxide and 80 ml of N,N-dimethylformamide to give 2.0 g of the intended product.

m.p. 147.0°–148.0° C.

$^1$H-NMR (CDCl$_3$, δ, TMS); 2.37 (3H, s), 5.58 (2H, s), 6.71 (1H, d, J=3 Hz), 7.07 (1H, d, J=3 Hz), 8.50 (1H, s).

SYNTHESIS EXAMPLE 13

Synthesis of 4-chloro-2-(4-chlorophenyl)-5-(2,4-dichlorobenzyloxy)-3(2H)-pyridazinone (Compound No. 39)

In 50 ml of N,N-dimethylformamide were dissolved 1.5 g (5.9 m mol) of 4-chloro-2-(4-chlorophenyl)-5-hydroxy-3(2H)-pyridazinone and 1.3 g (6.6 m mol) of 2,4-dichlorobenzyl chloride, and thereto was added 0.7 g of triethylamine. The reaction mixture was heated under stirring on an oil bath at 100° to 120° C. for 7 hours. After allowing to cool, the reaction mixture was poured into 200 ml of water and the precipitated solid was taken out by filtration, washed with water, dried and then recrystallized from benzene to give 1.7 g of the intended compound.

m.p. 168.0°–169° C.

$^1$H-NMR (CDCl$_3$, δ, TMS); 5.53 (2H, s), 7.28–7.78 (7H, m), 8.45 (1H, s).

SYNTHESIS EXAMPLE 14

Synthesis of 2-(4-chlorophenyl)-5-(2,4-dichlorobenzyloxy)-4-methoxy-3(2H)-pyridazinone (Compound No. 311)

In 60 ml of toluene was dissolved 1.0 g (2.4 m mol) of the 4-chloro-2-(4-chlorophenyl)-5-(2,4-dichlorobenzyloxy)-3(2H)-pyridazinone obtained in Synthesis Example 13, and 0.13 g (2.4 m mol) of sodium methoxide was added thereto. The resulting reaction liquid was refluxed under stirring for 12 hours. After allowing to cool, the reaction liquid was washed with water, dried over anhydrous sodium sulfate and freed of toluene by distillation to give a crude product. The crude product was purified through column chromatography (eluting with benzene/ethyl acetate=18/1) to obtain 450 mg of the intended compound.

m.p. 148.0°–150.0° C.

$^1$H-NMR (CDCl$_3$, δ, TMS); 4.01 (3H, s), 5.33 (2H, s), 7.08–7.63 (7H, m), 7.60 (1H, s).

SYNTHESIS EXAMPLE 15

Synthesis of 5-(4-chlorobenzyloxy)-2-(4-chlorophenyl)-3(2H)-pyridazinone (Compound No. 305)

In 50 ml of N,N-dimethylformamide were dissolved 2.0 g (9.0 m mol) of 2-(4-chlorophenyl)-5-hydroxy-3(2H)-pyridazinone and 1.5 g (9.3 m mol) of p-chlorobenzyl chloride, and thereto was added 1.7 g of anhydrous potassium carbonate. The reaction mixture was heated under stirring on an oil bath at 100°–120° C. for one hour. Then, the procedure in Synthesis Example 13 were repeated to give 2.5 g of the intended compound.

m.p. 203.0–204.0.

$^1$H-NMR (CDCl$_3$, δ, TMS); 5.05 (2H, s), 6.36 (1H, d, J=3Hz), 7.40–7.80 (8H, m), 7.90 (1H, d, J=3Hz).

SYNTHESIS EXAMPLE 16

Synthesis of 4-chloro-2-(3,4-dichlorophenyl)-5-(6-iodo-3-pyridyl)-methoxy)-3(2H)-pyridazinone (Compound No. 828)

The procedures in Synthesis Example 2 were repeated by using 3.10 g (10 m mol) of 2-(3,4-dichlorophenyl)-4,5-dichloro-3(2H)-pyridazinone, 2.47 g (10 m mol) of 6-iodo-3-pyridine-methanol, 0.75 g of potassium hydroxide and 60 ml of N,N-dimethylformamide to give 4.50 g of the intended product. (recrystallized from benzene)

m.p. 195.0°–196.0° C.

$^1$H-NMR (CDCl$_3$, δ, TMS); 5.33 (2H, s), 7.35–7.76 (4H, m), 7.88 (1H, dd, J=2Hz 8Hz), 7.94 (1H, s), 8.45 (1H, d, J=2Hz).

SYNTHESIS EXAMPLE 17

Synthesis of 2-(4-chlorophenyl)-5-{(6-chloro-3-pyridyl)-methoxy}-4-iodo-3(2H)-pyridazinone (Compound No. 831)

The procedures in Synthesis Example 2 were repeated by using 3.3 g (7.2 m mol) of 2-(4-chlorophenyl)-4,5-diiodo-3(2H)-pyridazinone, 1.1 g (7.7 m mol) of 6-chloro-3-pyridine-methanol, 0.4 g of potassium hydroxide and 80 ml of N,N-dimethylformamide to give 2.1 g of the intended product. (recrystallized from benzene)

m.p. 194.9°–195.5° C.

$^1$H-NMR (DMSO-d$^6$, δ, TMS); 5.52 (2H, s), 7.28–7.70 (5H, m), 7.83–8.15 (2H, m), 8.58 (1H, d, J=2Hz).

In accordance with any one of the procedures in Synthesis Examples 1 through 17, some compounds were prepared. The melting point each of these compounds is shown in Tables 1-a and 1-b.

When the compounds according to the present invention are used for insecticidal agents, they are generally mixed with appropriate carriers, for instance, solid carriers such as clay, talc, bentonite or diatomaceous earth, or liquid carriers such as water, alcohols (e.g., methanol and ethanol), aliphatic hydrocarbons, aromatic hydrocarbons (e.g., benzene, toluene and xylene), chlorinated hydrocarbons, ethers, ketones, esters (e.g., ethyl acetate), acid amides (e.g., dimethylformamide) or nitriles. If desired, to these mixtures may be added emulsifier, dispersing agent, suspension agent, penetrating agent, spreader, stabilizer, synergist and the like to put them into practical uses in the form of oil solution, emulsifiable concentrate, wettable powder, dust, granule, tablet, paste, flowable or the like.

Moreover, the mixtures may be incorporated with other insecticides, various fungicides, herbicides, plant-growth regulating agents, fertilizer and/or synergists during preparation or application thereof, as necessary.

The amount of the compounds of the invention to be used as an active ingredient is suitably in the range of 0.005 to 50 kg per hectare although it varies depending upon the place and the season where the compounds are applied, manner of application, diseases and insect pests to be applied, cultivated crops to be protected and the like.

The amount of the compounds of the invention contained in an insecticidal agent is desirably in the range of 0.01 to 99.5% by weight although it is not particularly restricted.

In the following, there are shown formulation examples of insecticidal compositions, said compositions containing the compounds of the present invention as an active ingredient. These examples are only illustrative and not to restrict the invention. In the following formulation example, "part" means "part by weight".

| Formulation Example 1: Emulsifiable concentrates | |
|---|---|
| Active ingredient | 10 parts |
| Xylene | 60 parts |
| N,N—dimethylformamide | 20 parts |
| Solpol 2680 (trade name, a mixture of a non-ionic surface-active agent and an anionic surface-active agent manufactured by Toho Chemicals, Co., Ltd, Japan) | 10 parts 10 parts |

The above components are mixed intimately together to form an emulsifiable concentrate. Upon use, the emulsifiable concentrate is diluted with water up to one fiftieth to one twenty thousandth in concentration and applied at a rate of 0.005 to 50 kg of the active ingredient per hectare.

| Formulation Example 2: Wettable powders | |
|---|---|
| Active ingredient | 10 parts |
| Siegreit PFP (trade name, a mixture of caolinite and sericite manufactured by Siegreit Mining Industries Co., Ltd.) | 81 parts |
| Solpol 5039 (trade name, anionic surface-active agent manufactured by Toho Chemical, Co., Ltd., Japan) | 4 parts |
| Carplex No. 80 (trade name, white carbon manufactured by Shionogi Seiyaku K. K., Japan) | 3 parts |
| Calcium lignin sulfonate | 2 parts |

The above components are homogeneously mixed together and ground to form a wettable powder. Upon use, the wettable powder is diluted with water up to one fiftieth to one twenty thousandth and applied at a rate of 0.005 to 50 kg of the active ingredient per hectare.

| Formulation Example 3: Oil solutions | |
|---|---|
| Active ingredient | 5 parts |
| methylcellosolve | 95 parts |

The above components are homogeneously mixed together to form an oil solution. Upon use, the oil solution is applied at a rate of 0.005 to 50 kg of the active ingredient per hectare.

| Formulation Example 4: Dusts | |
|---|---|
| Active ingredient | 3 parts |
| Carplex No. 80 (trade name) | 0.5 parts |
| Clay | 95 parts |
| di-isopropyl phosphate | 1.5 parts |

The above components are homogeneously mixed together and ground to form a dust. Upon use, the dust is applied at a rate of 0.005 to 50 kg of the active ingredient per hectare.

| Formulation Example 5: Granules | |
|---|---|
| Active ingredient | 5 parts |
| Bentonite | 54 parts |
| Talc | 40 parts |
| Calcuim lignin sulfonate | 1 parts |

The above components are mixed intimately together and ground, incorporated with a small amount of water and mixed together with stirring. The resulting mixture is granulated by means of extrusion-granulator and dried to form granules. Upon use, the granule is applied at a rate of 0.005 to 50 kg of the active ingredient per hectare.

| Formulation Example 6: Flowables | |
|---|---|
| Active ingredient | 25 parts |
| Solpol 3353 (trade name, a non-ionic surface-active agent manufactured by Toho Chemcials, Co., Ltd., Japan) | 10 parts |
| Runox 1000C (trade name, an anionic surface-active agent manufactured by Toho Chemicals, Co., Ltd. Japan) | 0.5 parts |
| 1% aqueous solution of Xanthan gum (natural high-molecular compound) | 20 parts |
| Water | 44.5 parts |

The above components except the active ingredient are uniformly mixed together to form a solution, and thereto is added the active ingredient. The resulting mixture is thoroughly stirred, wet-ground by means of sand mill to form a flowable. Upon use, the flowable is diluted up to one fiftieth to one twenty thousandth with water and applied at a rate of 0.005 to 50 kg of the active ingredient per hectare.

The compounds of the invention exhibit specific insecticidal action on hemiptera insects such as planthopper and leafhopper; Coleoptera insects such as red flour beetle (*Tribolium castaneum*), yellow mealworm (*Tenebrio molitor*) and 28-spotted lady beetle (*Henosepilachna vigintioctopunctata*); sanitary insect pests such as flies and mosquitos; and lepidoptera insects and also exhibit excellent residual action. Thus, the compounds of the invention provide an excellent insecticide which exhibits highly effective control of insect pests.

In the following, the effects of the present compounds as an insecticide are explained in detail by way of the test examples.

TEST EXAMPLE 1

Insecticidal Test on Green Rice Leafhopper
(*Nephotettix cincticeps*)

A 10% emulsifiable concentrate (or a 10% wettable powder) of a compound of the invention was diluted with water containing a spreader to give a 500 ppm solution of the compound. The stems and leaves of rice-plant in a 1/20000 are pot were sufficiently applied with the resulting solution and then air-dried. Thereafter, 20 second instar green rice hoppers (*Nephotettix cincticeps*) which resist organic phosphorous insecticides and carbamate insecticides were released in the pot.

The rice-plant thus treated was covered with a cylindrical wire gauze and kept in a thermostatic chamber. Thirty (30) days after, the number of the green rice leafhopper parasitic on the rice-plant was counted and the mortality thereof was determined according to the following equation:

Mortality (%) =

$$\frac{\text{number of the insect released} - \text{number of the insect parasitic on the rice-plant (number of the insect not killed)}}{\text{number of the insect released}} \times 100$$

The test was conducted twice for each compound. The results thereof are shown in Table 2.

TEST EXAMPLE 2

Insecticidal Test on Brown Rice Planthopper (*Nilaparvata lugens*)

The procedures in Test Example 1 were repeated by using second instar brown rice planthoppers (*Nilaparvata lugens*) instead of the second instar green rice leafhoppers which resist organic phosphorous insecticides and carbamate insecticides. The results thereof are shown in Table 3.

TEST EXAMPLE 3

Insecticidal Test on Red Flour Beetle (*Tribolium castaneum*)

In a transparent spitch tube was placed 50 mg of a 10% emulsifiable concentrate of a compound of the invention (or a 10% wettable powder or a 10% oil solution thereof), and thereto was added acetone to give a 500 ppm acetone solution of the compound. Ten (10) cc of the acetone solution was added to 10 g of wheat flour placed in a laboratory dish of 9 cm in diameter. After stirring acetone was distilled away from the mixture. Then, 10 adults each of male and female red flour beetles (*Tribolium castaneum*) were released in the dish. The dish containing the adults was kept in a thermostatic chamber. Ninety days after, evaluation was conducted by counting the number of the adults which came out.

The test was conducted twice for each compound. As a result, no hatched adult was observed at all in the dish treated with any one of the following compounds: Compound Nos. 27, 28, 175, 235, 283, 342, 584, 827, 828, 829, 830, 831, 834, 835, 837, 839 and 858.

TEST EXAMPLE 4

Fish-toxicity test on killifish

A methanol solution containing a compound of the invention to be tested is added to 2 l of water in a glass vessel of 20 cm in diameter and 10 cm in height to give a 0.5 ppm solution of the compound. The vessel was kept in a thermostatic chamber at 25° C. and then 10 killifishes were placed therein. The fish was observed with the passage of time. The mortality thereof after 48 hours is shown in Table 4.

TEST EXAMPLE 5

Acute Oral Toxicity Test to Mammals

ICR (Swiss Hauschka, CD-1, Ha/ICR) male mice were obtained at 4 weeks old from Clea Japan, Inc., and used in the tests after an acclimatizing period of one week. The animals in groups of 5 were housed in stainless cages with a wire-meshed bottom. The animals rooms were sustained in a barrier system with a controlled temperature of 22°±1° C., humidity of 55±5% and light for 12 hours a day. The animals were supplied food (CE-2, Clea Japan, Jinc.) and tap water ad libitum, Groups of 5 animals were administered a single oral dose of 300 mg/kg of the present inventional compound by oral gavage. The compounds were diluted by corn oil, and all administration volumes were 10 ml/kg body weight. The mortalities were calculated seven days after oral administration. The result was shown in Table 5.

TEST EXAMPLE 6

Insecticidal Test on Almond Moth (*Ephestia cautella*)

In a transparent spitch tube was placed 50 mg of a emulsifiable concentrate of a compound of the invention (or a wettable powder or an oil solution thereof), and thereto was added acetone to give a 500 ppm acetone solution of the compound. Ten (10) cc of the acetone solution was added to 10 g of rice bran placed in a laboratory dish of 9 cm in diameter. After stirring acetone was distilled away from the mixture. Then, 10 larvae each of almond moth (*Ephestia cautella*) were released in the dish. The dish containing the larvae was kept in a thermostatic chamber. 30 days after, evaluation was conducted by counting the number of the adults which came out.

The test was conducted twice for each compound. As a result, no hatched adult was observed at all in the dish treated with any one of the following compounds: Compound Nos. 340, 341, 342, 584, 590, 778, 802, 827, 828, 829, 831, 834, 837 and 858.

In the following Table, Me represents methyl, Et represents ethyl, Pro represents propyl, Bu represents butyl, Pen represents pentyl, Hex represents hexyl, t represents tertiary, i represents iso, and s represents secondary.

TABLE 1-a

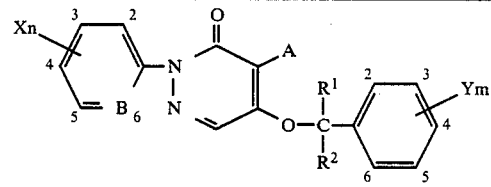

| Compound No. | $R^1$ | $R^2$ | $X_n$ | $Y_m$ | B | A | m.p. (°C.) |
|---|---|---|---|---|---|---|---|
| 1 | H | H | 2-Cl | 4-Me | CH | Cl | 173.0~174.2 |
| 2 | Me | H | 2-Cl | 2-Me | CH | Cl | |
| 3 | H | H | 2-Cl | 4-s-Bu | CH | Cl | |
| 4 | H | H | 2-Cl | 4-Cl | CH | Cl | 187.1~187.9 |
| 5 | H | H | 2-Cl | 4-Br | CH | Cl | 187.6~189.0 |
| 6 | H | H | 2-Cl | 3-CF$_3$ | CH | Cl | |
| 7 | H | H | 2-Cl | 4-OMe | CH | Br | |

TABLE 1-a-continued

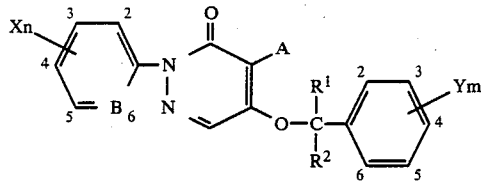

| Compound No. | R¹ | R² | $X_n$ | $Y_m$ | B | A | m.p. (°C.) |
|---|---|---|---|---|---|---|---|
| 8 | H | H | 2-Cl | 3-O—i-Pro | CH | Br | |
| 9 | H | H | 3-Cl | 4-Me | CH | Cl | |
| 10 | H | H | 3-Cl | 4-Pen | CH | Cl | |
| 11 | H | H | 3-Cl | 3-Cl | CH | Cl | |
| 12 | H | H | 3-Cl | 4-Cl | CH | Cl | 166.0~167.0 |
| 13 | Me | H | 3-Cl | 4-Br | CH | Cl | |
| 14 | H | H | 3-Cl | 4-t-Bu | CH | Cl | 192.0~194.0 |
| 15 | H | H | 3-Cl | 4-OEt | CH | Br | |
| 16 | H | H | 3-Cl | 4-OPro | CH | Cl | |
| 17 | H | H | 3-Cl | 2,5-(Me)₂ | CH | Cl | |
| 18 | H | H | 3-Cl | 2,4-Cl₂ | CH | Cl | |
| 19 | H | H | 3-Cl | 3,4-Cl₂ | CH | Br | |
| 20 | H | H | 4-Cl | 4-C₆H₅ | CH | Cl | 213.3~220.0 |
| 21 | Me | H | 4-Cl | 4-(4-ClC₆H₄) | CH | Cl | |
| 22 | H | H | 4-Cl | 4-Me | CH | Cl | 214.0~216.0 |
| 23 | H | H | 4-Cl | 4-i-Bu | CH | Cl | |
| 24 | H | H | 4-Cl | 3-Me | CH | Cl | |
| 25 | H | H | 4-Cl | 2-Me | CH | Cl | |
| 26 | Me | H | 4-Cl | 2-Me | CH | Cl | |
| 27 | H | H | 4-Cl | 4-Cl | CH | Cl | 184.5~186.0 |
| 28 | H | H | 4-Cl | 4-Cl | CH | Br | 168.5~175.1 |
| 29 | Me | H | 4-Cl | 4-Cl | CH | Cl | 135.0~138.0 |
| 30 | H | H | 4-Cl | 3-Cl | CH | Cl | |
| 31 | H | H | 4-Cl | 3-Cl | CH | Br | |
| 32 | H | H | 4-Cl | 2-Cl | CH | Cl | |
| 33 | H | H | 4-Cl | 4-Br | CH | Cl | 184.6~185.7 |
| 34 | H | H | 4-Cl | 4-Br | CH | Br | 187.1~187.9 |
| 35 | H | H | 4-Cl | 4-I | CH | Cl | 195.0~196.5 |
| 36 | H | H | 4-Cl | 2,5-(Me)₂ | CH | Cl | 204.0~206.0 |
| 37 | H | H | 4-Cl | 4-t-Bu | CH | Cl | 238.9~240.2 |
| 38 | H | H | 4-Cl | 3,4-Cl₂ | CH | Cl | 194.0~196.0 |
| 39 | H | H | 4-Cl | 2,4-Cl₂ | CH | Cl | 168.0~169.0 |
| 40 | H | H | 4-Cl | 4-F | CH | Cl | |
| 41 | H | H | 4-Cl | 2,6-(Me)₂, 4-t-Bu | CH | Cl | |
| 42 | H | H | 4-Cl | 2,3,4,5,6-F₅ | CH | Cl | |
| 43 | H | H | 4-Cl | 3-OBu | CH | Cl | |
| 44 | H | H | 4-Cl | 4-O—s-Bu | CH | Cl | |
| 45 | H | H | 4-Cl | 4-(C₆H₅CH₂O) | CH | Cl | 188.0~190.0 |
| 46 | H | H | 4-Cl | 4-(2-MeC₆H₄CH₂O) | CH | Cl | |
| 47 | H | H | 4-Cl | 4-(3,4-Cl₂C₆H₃CH₂O) | CH | Br | |
| 48 | H | H | 4-Cl | 4-(4-FC₆H₄CH₂O) | CH | Cl | |
| 49 | H | H | 4-Cl | 4-CF₃ | CH | Cl | 186.0~188.0 |
| 50 | H | H | 4-Cl | 3-CF₃ | CH | Br | |
| 51 | H | H | 4-Cl | 4-OCHF₂ | CH | Cl | 177.4~178.4 |
| 52 | H | H | 4-Cl | 4-OCF₃ | CH | Cl | |
| 53 | Et | H | 4-Cl | 4-Cl | CH | Cl | |
| 54 | H | H | 4-Cl | 4-OCH₂CF₃ | CH | Cl | |
| 55 | H | H | 4-Cl | 4-CN | CH | Br | 218.2~219.4 |
| 56 | H | H | 2-Me | 4-F | CH | Cl | 182.0~184.0 |
| 57 | H | H | 2-Me | 4-Cl | CH | Cl | 166.0~168.0 |
| 58 | H | H | 2-Me | 3-Cl | CH | Br | |
| 59 | H | H | 2-Me | 4-Br | CH | Cl | 166.0~167.0 |
| 60 | Me | H | 2-Me | 4-I | CH | Cl | |
| 61 | H | H | 2-Me | 4-Me | CH | Cl | 145.0~146.0 |
| 62 | H | H | 2-Me | 4-i-Pro | CH | Cl | 139.0~140.0 |
| 63 | H | H | 2-Me | 4-O—i-Pro | CH | Br | |
| 64 | H | H | 2-Me | 4-(2,4-Cl₂C₆H₃) | CH | Cl | |
| 65 | H | H | 2-Me | 3-(2,4-Cl₂C₆H₃CH₂O) | CH | Br | |
| 66 | H | H | 2-Me | 4-CF₃ | CH | Cl | |
| 67 | H | H | 2-Me | 4-OCHF₂ | CH | Cl | |
| 68 | H | H | 3-Me | 3-Me | CH | Cl | 154.4~155.8 |
| 69 | H | H | 3-Me | 4-Cl | CH | Cl | 176.0~177.0 |
| 70 | Me | H | 3-Me | 4-Br | CH | Cl | |
| 71 | H | H | 3-Me | 4-Me | CH | Cl | 126.0~127.0 |
| 72 | Me | H | 3-Me | 2-Cl | CH | Cl | |
| 73 | Me | H | 3-Me | 2,4-Cl₂ | CH | Br | |
| 74 | Et | H | 3-Me | 3,4-Cl₂ | CH | Cl | |
| 75 | H | H | 3-Me | 4-CH₃ | CH | Cl | |
| 76 | H | H | 3-Me | 4-i-Pro | CH | Cl | 137.0~138.0 |
| 77 | H | H | 3-Me | 3-CF₃ | CH | Br | |
| 78 | H | H | 3-Me | 4-OBu | CH | Cl | |

TABLE 1-a-continued

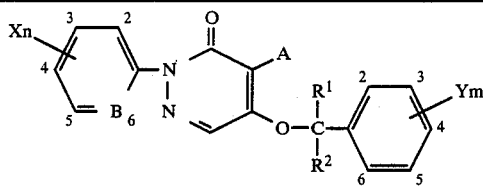

| Compound No. | R¹ | R² | Xₙ | Yₘ | B | A | m.p. (°C.) |
|---|---|---|---|---|---|---|---|
| 79 | H | H | 4-Me | 4-t-Bu | CH | Cl | 190.9~191.9 |
| 80 | Pro | H | 4-Me | 4-Me | CH | Cl | |
| 81 | H | H | 4-Me | 3,4-Cl₂ | CH | Cl | 218.0~220.0 |
| 82 | H | H | 4-Me | 4-Br | CH | Cl | 225.0~226.0 |
| 83 | H | H | 4-Me | 4-Cl | CH | Cl | |
| 84 | H | H | 4-Me | 3-Cl | CH | Cl | 196.0~197.0 |
| 85 | Me | H | 4-Me | 4-(4-ClC₆H₄) | CH | Cl | |
| 86 | H | H | 4-Me | 4-OMe | CH | Br | |
| 87 | H | H | 4-Me | 4-OCF₃ | CH | Cl | |
| 88 | H | H | 4-Me | 2,4-Cl₂ | CH | Cl | 164.0~165.0 |
| 89 | H | H | 4-Me | 2,4-(Me)₂ | CH | Cl | 156.0~157.0 |
| 90 | H | H | 4-Me | 2,5-(Me)₂ | CH | Cl | 173.0~175.0 |
| 91 | H | H | 4-Me | 3-OMe, 4-OPro | CH | Cl | |
| 92 | H | H | 4-Br | 4-Me | CH | Cl | |
| 93 | H | H | 4-Br | 2-Me | CH | Cl | |
| 94 | H | H | 4-Br | 4-t-Bu | CH | Br | |
| 95 | Me | H | 4-Br | 4-Hex | CH | Cl | |
| 96 | Et | H | 4-Br | 4-t-Bu | CH | Cl | |
| 97 | H | H | 4-Br | 4-Cl | CH | Cl | 190.0~191.0 |
| 98 | H | H | 4-Br | 4-Br | CH | Cl | |
| 99 | Me | H | 4-Br | 4-(4-MeC₆H₄) | CH | Br | |
| 100 | H | H | 4-Br | 3-OBu | CH | Cl | |
| 101 | H | H | 4-Br | 4-OCHF₂ | CH | Cl | |
| 102 | H | H | 4-Br | 4-CF₃ | CH | Cl | |
| 103 | Me | H | 3-CF₃ | 4-Me | CH | Cl | |
| 104 | Et | H | 3-CF₃ | 4-t-Bu | CH | Br | |
| 105 | Me | H | 3-CF₃ | 4-Cl | CH | Cl | |
| 106 | Me | H | 3-CF₃ | 4-Br | CH | Cl | |
| 107 | Me | H | 3-CF₃ | 2,4-Cl₂ | CH | Cl | |
| 108 | H | H | 4-CF₃ | 4-F | CH | Cl | |
| 109 | H | H | 4-CF₃ | 4-Cl | CH | Cl | 171.0~175.0 |
| 110 | H | H | 4-CF₃ | 4-Cl | CH | Br | |
| 111 | H | H | 4-CF₃ | 4-Br | CH | Cl | |
| 112 | H | H | 4-CF₃ | 4-Br | CH | Br | |
| 113 | Pro | H | 4-CF₃ | 4-Me | CH | Cl | |
| 114 | Me | H | 4-CF₃ | 4-(4-ClC₆H₄) | CH | Cl | |
| 115 | H | H | 4-CF₃ | 4-O—i-Pro | CH | Br | |
| 116 | H | H | 4-CF₃ | 4-(4-MeC₆H₄CH₂O) | CH | Cl | |
| 117 | H | H | 4-CF₃ | 4-OCHF₂ | CH | Cl | |
| 118 | H | H | 4-CF₃ | 4-OCHF₂ | CH | Br | |
| 119 | H | H | 4-CF₃ | 4-OCH₂CF₃ | CH | Cl | |
| 120 | H | H | 4-CF₃ | 4-CF₃ | CH | Cl | |
| 121 | H | H | 4-CF₃ | 4-CF₃ | CH | Br | |
| 122 | H | H | 4-CF₃ | 2,4-Cl₂ | CH | Cl | |
| 123 | H | H | 4-CF₃ | 3,4-Cl₂ | CH | Cl | |
| 124 | H | H | 4-CF₃ | 2,4-(Me)₂ | CH | Cl | |
| 125 | H | H | 4-CF₃ | 2,6-(Me)₂ 4-t-Br | CH | Cl | |
| 126 | H | H | 4-CF₃ | 2,3,4,5,6-F₅ | CH | Cl | |
| 127 | H | H | 4-CF₃ | 2,3,4,5,6-F₅ | CH | Br | |
| 128 | H | H | 4-CF₃ | 4-CN | CH | Cl | |
| 129 | H | H | 2-Et | 4-Me | CH | Cl | |
| 130 | H | H | 2-Et | 4-Cl | CH | Cl | |
| 131 | H | H | 3-Et | 4-CF₃ | CH | Cl | |
| 132 | H | H | 4-Et | 4-OCHF₂ | CH | Cl | |
| 133 | H | H | 4-Et | 4-Cl | CH | Cl | |
| 134 | H | H | 4-i-Pro | 2-Cl | CH | Br | |
| 135 | Me | H | 4-Bu | 4-Cl | CH | Cl | |
| 136 | H | H | 4-OCHF₂ | 4-Cl | CH | Cl | |
| 137 | H | H | 4-OCHF₂ | 4-Cl | CH | Br | |
| 138 | H | H | 4-OCHF₂ | 3-CF₃ | CH | Cl | |
| 139 | H | H | 4-OCHF₂ | 4-CF₃ | CH | Cl | |
| 140 | H | H | 4-OCHF₂ | 4-OCHF₂ | CH | Cl | |
| 141 | H | H | 4-OCHF₂ | 4-OCH₃ | CH | Cl | |
| 142 | H | H | 4-OCHF₂ | 4-Br | CH | Br | |
| 143 | H | H | 4-OCHF₂ | 4-Br | CH | Cl | |
| 144 | Me | H | 4-OCHF₂ | 4-(4-ClC₆H₄) | CH | Cl | |
| 145 | H | H | 2-Cl, 4-Me | 4-OCHF₂ | CH | Cl | |
| 146 | H | H | 2-Cl, 4-Me | 4-(4-ClC₆H₄) | CH | Cl | |
| 147 | H | H | 2-F, 4-Me | 4-Cl | CH | Cl | |
| 148 | H | H | 2-F, 4-Me | 3-O—Bu | CH | Br | |
| 149 | H | H | 2-F, 4-Me | 4-OCHF₂ | CH | Cl | |

TABLE 1-a-continued

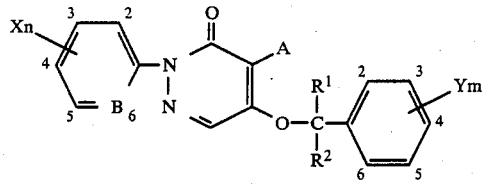

| Compound No. | R¹ | R² | Xₙ | Yₘ | B | A | m.p. (°C.) |
|---|---|---|---|---|---|---|---|
| 150 | H | H | 2,4-Br₂ | 2-CH₃ | CH | Br | |
| 151 | H | H | 2,4-Br₂ | 4-Cl | CH | Cl | |
| 152 | H | H | 2,4-Br₂ | 4-CF₃ | CH | Cl | |
| 153 | H | H | 2,4-Br₂ | 4-Cl | CH | Cl | |
| 154 | H | H | 2,4-F₂ | 4-Cl | CH | Cl | 166.6~166.9 |
| 155 | H | H | 2,4-F₂ | 4-Cl | CH | Br | |
| 156 | H | H | 2,4-F₂ | 4-Br | CH | Cl | |
| 157 | H | H | 2,4-F₂ | 4-(4-ClC₆H₄) | CH | Cl | |
| 158 | H | H | 2,4-F₂ | 4-OCHF₂ | CH | Cl | |
| 159 | H | H | 2,4-F₂ | 4-OCHF₂ | CH | Br | |
| 160 | H | H | 2,4-F₂ | 4-CF₃ | CH | Cl | |
| 161 | H | H | 2,4-F₂ | 4-CF₃ | CH | Br | |
| 162 | H | H | 2,6-F₂ | 4-Cl | CH | Cl | |
| 163 | H | H | 2,6-F₂ | 3,4,5-(MeO)₃ | CH | Cl | |
| 164 | H | H | 4-Br, 2-Cl | 4-CF₃ | CH | Cl | |
| 165 | H | H | 4-Br, 2-Cl | 3-CF₃ | CH | Br | |
| 166 | H | H | 4-Br, 2-F | 4-Cl | CH | Cl | 180.0~181.0 |
| 167 | H | H | 4-Br, 2-F | 4-Cl | CH | Br | 180.0~181.0 |
| 168 | H | H | 4-Br, 2-F | 4-OCHF₂ | CH | Cl | |
| 169 | H | H | 4-Br, 2-F | 4-(4-ClC₆H₄) | CH | Cl | |
| 170 | H | H | 4-Cl, 2-F | 4-Cl | CH | Cl | 167.3~167.9 |
| 171 | H | H | 4-Cl, 2-F | 4-Cl | CH | Br | 166.0~168.0 |
| 172 | H | H | 4-Cl, 2-F | 4-Br | CH | Cl | 160.0~162.0 |
| 173 | H | H | 4-Cl, 2-F | 4-Br | CH | Br | |
| 174 | H | H | 4-Cl, 2-F | 4-F | CH | Cl | 172.4~173.0 |
| 175 | H | H | 4-Cl, 2-F | 4-Me | CH | Cl | 172.0~173.0 |
| 176 | H | H | 4-Cl, 2-F | 4-CF₃ | CH | Cl | |
| 177 | H | H | 4-Cl, 2-F | 4-CF₃ | CH | Br | |
| 178 | H | H | 4-Cl, 2-F | 4-OCHF₂ | CH | Cl | 164.0~165.2 |
| 179 | H | H | 4-Cl, 2-F | 4-OCHF₂ | CH | Br | |
| 180 | H | H | 4-Cl, 2-F | 4-(4-ClC₆H₄) | CH | Cl | |
| 181 | | | 4-Cl, 2-F | 4-(4-ClC₆H₄CH₂O) | CH | Cl | |
| 182 | H | H | 4-Cl, 2-F | 4-CN | CH | Cl | |
| 183 | H | H | 3-Cl, 2-F | 4-Cl | CH | Cl | |
| 184 | H | H | 3-Cl, 2-F | 4-CF₃ | CH | Cl | |
| 185 | H | H | 2-Cl, 4-CF₃ | 4-Cl | CH | Cl | |
| 186 | H | H | 2-Cl, 4-CF₃ | 4-Cl | CH | Br | |
| 187 | H | H | 2-Cl, 4-CF₃ | 4-OCHF₂ | CH | Cl | |
| 188 | H | H | 2-Cl, 4-CF₃ | 4-OCHF₂ | CH | Br | |
| 189 | H | H | 2,4-Cl₂ | 4-Cl | CH | Cl | 184.0~185.0 |
| 190 | H | H | 2,4-Cl₂ | 4-Br | CH | Cl | 193.0~195.0 |
| 191 | H | H | 2,4-Cl₂ | 2-Me | CH | Cl | |
| 192 | H | H | 2,3,4-Cl₃ | 4-OCH₂CF₃ | CH | Cl | |
| 193 | H | H | 2,4,5-Cl₃ | 4-CN | CH | Cl | |
| 194 | H | H | 2,4,6-Cl₃ | 4-t-Bu | CH | Br | |
| 195 | Me | H | 2,4,6-Br₃ | 3,4-Cl₂ | CH | Cl | |
| 196 | Me | H | 2,4,6-Br₃ | 2-Me | CH | Cl | |
| 197 | H | H | 2,4,6-F₃ | 4-Cl | CH | Cl | |
| 198 | H | H | 2,4,6-F₃ | 4-Br | CH | Cl | |
| 199 | H | H | 2,4,6-F₃ | 4-CF₃ | CH | Cl | |
| 200 | H | H | 2,4,6-F₃ | 4-CF₃ | CH | Br | |
| 201 | H | H | 4-Cl, 2,6-F₂ | 4-Cl | CH | Cl | |
| 202 | H | H | 4-Cl, 2,6-F₂ | 4-OCF₃ | CH | Cl | |
| 203 | H | H | 4-Br, 2,3-Cl₂ | 3-(2,4-Cl₂C₆H₃CH₂O) | CH | Cl | |
| 204 | Me | H | 4-Br, 2,6-Cl₂ | 4-F | CH | Cl | |
| 205 | H | H | 2,3,4,5-F₄ | 4-Cl | CH | Cl | |
| 206 | H | H | 2,3,4,5-F₄ | 4-OCHF₂ | CH | Cl | |
| 207 | H | H | 2,3,4,6-F₄ | 4-Cl | CH | Cl | |
| 208 | Me | H | 2,3,4,6-F₄ | 2,4-Cl₂ | CH | Cl | |
| 209 | H | H | 2,3,5,6-F₄ | 4-CN | CH | Cl | |
| 210 | H | H | 2,3,5,6-F₄ | 4-Cl | CH | Cl | |
| 211 | H | H | 2,3,4,5-Cl₄ | 4-C₆H₅ | CH | Br | |
| 212 | H | H | 2,3,5,6-Cl₄ | 4-OCH₂CF₃ | CH | Cl | |
| 213 | H | H | 2,4-Br₂, 5,6-Cl₂ | 4-CF₃ | CH | Br | |
| 214 | H | H | 2,3,4,5,6-F₅ | 4-Cl | CH | Cl | |
| 215 | H | H | 2,3,4,5,6-F₅ | 4-Cl | CH | Br | |
| 216 | H | H | 2,3,4,5,6-F₅ | 4-Br | CH | Cl | |
| 217 | Me | H | 2,3,4,5,6-F₅ | 4-t-Bu | CH | Cl | |
| 218 | Me | H | 2,3,4,5,6-F₅ | 4-CH₃ | CH | Cl | |
| 219 | H | H | 2,3,4,5,6-F₅ | 4-OCHF₂ | CH | Cl | |
| 220 | H | H | 2,3,4,5,6-F₅ | 4-CF₃ | CH | Cl | |

TABLE 1-a-continued

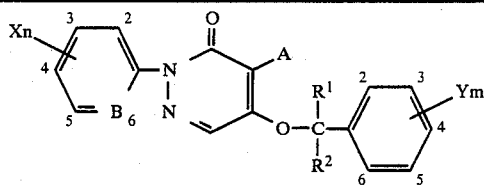

| Compound No. | R¹ | R² | $X_n$ | $Y_m$ | B | A | m.p. (°C.) |
|---|---|---|---|---|---|---|---|
| 221 | Me | H | 2,3,4,5,6-F₅ | 4-(2,4-Cl₂C₆H₃) | CH | Cl | |
| 222 | H | H | 2,3,4,5,6-F₅ | 2,5-(Me)₂ | CH | Cl | |
| 223 | H | H | 2,3,4,5,6-F₅ | 2,3,4,5,6-F₅ | CH | Cl | |
| 224 | H | H | 2-F | 4-Cl | CH | Cl | |
| 225 | H | H | 2-F | 4-Cl | CH | Br | |
| 226 | H | H | 2-F | 4-Br | CH | Cl | |
| 227 | H | H | 2-F | 4-Me | CH | Cl | |
| 228 | H | H | 2-F | 4-Hex | CH | Br | |
| 229 | Me | H | 2-F | 4-(4-ClC₆H₄) | CH | Cl | |
| 230 | H | H | 2-F | 4-CF₃ | CH | Cl | |
| 231 | H | H | 2-F | 4-CF₃ | CH | Br | |
| 232 | H | H | 2-F | 4-OCHF₂ | CH | Cl | |
| 233 | H | H | 2-F | 4-OCHF₂ | CH | Br | |
| 234 | H | H | 2-F | 4-CN | CH | Cl | |
| 235 | H | H | 4-Cl | 4-Cl | N | Cl | 166.7~169.0 |
| 236 | H | H | 4-Cl | 4-Cl | N | Br | |
| 237 | H | H | 4-Cl | 4-Br | N | Cl | |
| 238 | H | H | 4-Cl | 4-OCHF₂ | N | Cl | |
| 239 | H | H | 4-Cl | 4-CF₃ | N | Cl | |
| 240 | H | H | 4-Br | 4-Cl | N | Cl | |
| 241 | H | H | 4-Br | 4-Cl | N | Br | |
| 242 | H | H | 4-Br | 4-Br | N | Cl | |
| 243 | H | H | 4-Br | 4-OCHF₂ | N | Cl | |
| 244 | H | H | 4-CF₃ | 4-Cl | N | Cl | |
| 245 | H | H | 4-CF₃ | 4-Me | N | Cl | |
| 246 | H | H | 4-CF₃ | 4-CF₃ | N | Cl | |
| 247 | H | H | 4-CF₃ | 4-OCHF₃ | N | Cl | |
| 248 | Me | H | 2-Cl, 4-CF₃ | 4-(4-ClC₆H₄) | N | Cl | |
| 249 | H | H | 2-Cl, 4-CF₃ | 4-O—Pro | N | Cl | |
| 250 | H | H | 2-Cl, 4-CF₃ | 4-Cl | N | Cl | |
| 251 | H | H | 4-Cl, 2-CF₃ | 4-Cl | N | Cl | |
| 252 | H | H | 4-Cl, 2-CF₃ | 4-Cl | N | Br | |
| 253 | H | H | 4-Cl, 2-CF₃ | 4-F | N | Cl | |
| 254 | H | H | 4-Cl, 2-CF₃ | 3-CF₃ | N | Cl | |
| 255 | H | H | 4-Cl, 2-CF₃ | 4-OCHF₂ | N | Cl | |

TABLE 1-b

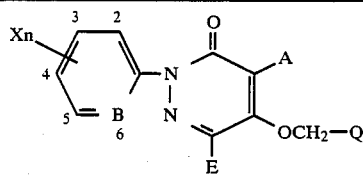

| Compound No. | $X_n$ | Q | E | B | A | m.p. (°C.) |
|---|---|---|---|---|---|---|
| 256 | 4-Cl | 2,4-Cl₂—C₆H₃ | H | CH | Br | 148.7~152.1 |
| 257 | 4-Cl | 4-I—C₆H₄ | H | CH | Br | |
| 258 | 4-Cl | 4-Me—C₆H₄ | H | CH | Br | |
| 259 | 4-Cl | 4-(4-FC₆H₄)C₆H₄ | H | CH | Br | 203.0~207.0 |
| 260 | 4-Cl | 2-Me, 4-Cl—C₆H₃ | H | CH | Cl | |
| 261 | 4-Cl | 2,4,6-Cl₃—C₆H₂ | H | CH | Cl | |
| 262 | 4-Cl | 2,4,6-Cl₃—C₆H₂ | H | CH | Br | |
| 263 | 4-Cl | 4-(4-ClC₆H₄CH₂O)C₆H₄ | H | CH | Cl | 190.0~191.5 |
| 264 | 4-Cl | 2,4,5-Cl₃—C₆H₂ | H | CH | Cl | |
| 265 | 4-Cl | 2,4-F₂C₆H₃ | H | CH | Br | 176.7~179.0 |
| 266 | 4-Cl | 2,4-F₂—C₆H₃ | H | CH | Cl | 180.6~185.8 |
| 267 | 4-Cl | 2,4,5-Cl₃—C₆H₂ | H | CH | Br | |
| 268 | 4-Cl | 2,6-Cl₂—C₆H₃ | H | CH | Cl | 201.0~203.0 |
| 269 | 4-Cl | 2-Me, 4-Br—C₆H₃ | H | CH | Br | |
| 270 | 4-Cl | 3,5-Cl₂—C₆H₃ | H | CH | Br | |
| 271 | 4-Cl | 2,3,4,5,6-F₅C₆ | H | CH | Br | |
| 272 | 4-Cl | 2-Cl, 4-F—C₆H₃ | H | CH | Cl | 193.7~194.6 |
| 273 | 4-Cl | 2-F, 4-Cl—C₆H₃ | H | CH | Cl | 176.2~178.1 |
| 274 | 4-Cl | 2-F, 4-Cl—C₆H₃ | H | CH | Br | 145.9~158.9 |
| 275 | 4-Cl | 4-Pro—C₆H₄ | H | CH | Br | |

TABLE 1-b-continued

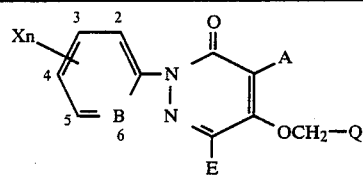

| Compound No. | $X_n$ | Q | E | B | A | m.p. (°C.) |
|---|---|---|---|---|---|---|
| 276 | 4-Cl | 2,5-Cl$_2$—C$_6$H$_3$ | H | CH | Cl | 176.0~180.0 |
| 277 | 4-Cl | 2-F, 4-Br—C$_6$H$_3$ | H | CH | Cl | 176.6~178.3 |
| 278 | 4-Cl | 2-F, 4-Br—C$_6$H$_3$ | H | CH | Br | 179.3~180.2 |
| 279 | 4-Cl | Q1 | H | CH | Br | |
| 280 | 4-Cl | 4-ProO—C$_6$H$_4$ | H | CH | Br | 170.0~171.0 |
| 281 | 4-Cl | 4-Hex—C$_6$H$_4$ | H | CH | Br | |
| 282 | 4-Cl | 2-Cl, 4-CF$_3$—C$_6$H$_3$ | H | CH | Br | |
| 283 | 4-Cl | 4-CF$_3$—C$_6$H$_4$ | H | CH | Br | 181.0~182.0 |
| 284 | 4-Cl | 2-Cl, 4-Br—C$_6$H$_3$ | H | CH | Cl | |
| 285 | 4-Cl | 2-Cl, 4-Br—C$_6$H$_3$ | H | CH | Br | |
| 286 | 4-Cl | 4-F—C$_6$H$_4$ | H | CH | Br | 174.0~175.5 |
| 287 | 4-Cl | 4-ClCH$_2$CH$_2$—C$_6$H$_4$ | H | CH | Cl | |
| 288 | 4-Cl | 2,6-F$_2$, 4-Cl—C$_6$H$_2$ | H | CH | Cl | |
| 289 | 4-Cl | 2,6-F$_2$, 4-Cl—C$_6$H$_2$ | H | CH | Br | |
| 290 | 4-Cl | Q2 | H | CH | Cl | |
| 291 | 4-Cl | 2,4-Cl$_2$, 6-F—C$_6$H$_2$ | H | CH | Cl | |
| 292 | 4-Cl | 2,6-F$_2$, 4-Br—C$_6$H$_2$ | H | CH | Cl | |
| 293 | 4-Cl | 2-Cl, 4-Me—C$_6$H$_3$ | H | CH | Cl | |
| 294 | 4-Cl | 2-F, 4-Me—C$_6$H$_3$ | H | CH | Br | |
| 295 | 4-Cl | 2-Me, 4-Cl—C$_6$H$_3$ | H | CH | Br | 179.3~179.7 |
| 296 | 4-Cl | 2-MeO, 4-Cl—C$_6$H$_3$ | H | CH | Br | |
| 297 | 4-Cl | Q36 | H | CH | Br | |
| 298 | 4-Cl | 4-Cl—C$_6$H$_4$ | OH | CH | Cl | |
| 299 | 4-Cl | 4-Cl—C$_6$H$_4$ | Cl | CH | Cl | |
| 300 | 4-Cl | 4-Cl—C$_6$H$_4$ | OCH$_3$ | CH | Cl | 176.0~178.0 |
| 301 | 4-Cl | 2,4-Cl$_2$—C$_6$H$_3$ | Cl | CH | Cl | |
| 302 | 4-Cl | 2,4-Cl$_2$—C$_6$H$_3$ | OCH$_3$ | CH | Cl | 146.0~149.0 |
| 303 | 4-Cl | 4-Br—C$_6$H$_4$ | OCH$_3$ | CH | Cl | |
| 304 | 4-Cl | 2-F, 4-Cl—C$_6$H$_3$ | Cl | CH | Cl | |
| 305 | 4-Cl | 4-Cl—C$_6$H$_4$ | H | CH | H | 203.0~204.0 |
| 306 | 4-Cl | 2,4-Cl$_2$—C$_6$H$_3$ | H | CH | H | 221.5~222.8 |
| 307 | 4-Cl | 2-F, 4-Cl—C$_6$H$_3$ | H | CH | H | |
| 308 | 4-Cl | 4-Cl—C$_6$H$_4$ | H | CH | OCH$_3$ | 149.0~150.8 |
| 309 | 4-Cl | 4-Br—C$_6$H$_4$ | H | CH | OCH$_3$ | |
| 310 | 4-Cl | 2-F, 4-Cl—C$_6$H$_3$ | H | CH | OCH$_3$ | |
| 311 | 4-Cl | 2,4-Cl$_2$—C$_6$H$_3$ | H | CH | OCH$_3$ | 148.0~150.0 |
| 312 | 4-Cl | 3-Cl—C$_6$H$_4$ | H | CH | Oi-Bu | |
| 313 | 4-Cl | 4-Pen—C$_6$H$_4$ | H | CH | OEt | |
| 314 | 4-Cl | 2,4-Cl$_2$—C$_6$H$_3$ | H | N | Br | |
| 315 | 4-Cl | 2-F, 4-Cl—C$_6$H$_3$ | H | N | Cl | |
| 316 | 4-Cl | 2-F, 4-Cl—C$_6$H$_3$ | H | N | Br | |
| 317 | 4-Cl | 4-Br—C$_6$H$_4$ | H | N | Br | |
| 318 | 4-Cl | 2,4-Cl$_2$—C$_6$H$_3$ | H | N | Cl | |
| 319 | 4-Cl | 4-Cl—C$_6$H$_4$ | H | N | H | |
| 320 | 4-Cl | Q3 | H | CH | Cl | |
| 321 | 4-Cl | Q3 | H | CH | Br | |
| 322 | 4-Cl | Q4 | H | CH | Cl | |
| 323 | 4-Cl | Q5 | H | CH | Cl | 147.0~148.0 |
| 324 | 4-Cl | Q6 | H | CH | Br | |
| 325 | 4-Cl | Q7 | H | CH | Cl | |
| 326 | 4-Cl | Q8 | H | CH | Cl | |
| 327 | 4-Cl | Q9 | H | CH | Br | |
| 328 | 4-Cl | Q10 | H | CH | Br | |
| 329 | 4-Cl | Q10 | H | CH | Cl | |
| 330 | 4-Cl | Q11 | H | CH | Br | |
| 331 | 4-Cl | Q12 | H | CH | Cl | |
| 332 | 4-Cl | Q13 | H | CH | Cl | |
| 333 | 4-Cl | Q14 | H | CH | Cl | |
| 334 | 4-Cl | Q12 | H | CH | Br | |
| 335 | 4-Cl | Q15 | H | CH | Cl | |
| 336 | 4-Cl | Q16 | H | CH | Cl | 135.0~136.5 |
| 337 | 4-Cl | Q17 | H | CH | Cl | 190.0~195.0 |
| 338 | 4-Cl | Q18 | H | CH | Br | |
| 339 | 4-Cl | Q19 | H | CH | Cl | |
| 340 | 4-Cl | Q20 | H | CH | Cl | 190.0~192.0 |
| 341 | 4-Cl | Q20 | H | CH | Br | 195.0~197.0 |
| 342 | 4-Cl | Q21 | H | CH | Cl | 197.0~198.0 |
| 343 | 4-Cl | Q21 | H | CH | Br | |
| 344 | 4-Cl | Q22 | H | CH | Cl | |
| 345 | 4-Cl | Q22 | H | CH | Br | |
| 346 | 4-Cl | Q23 | H | CH | Cl | |

TABLE 1-b-continued

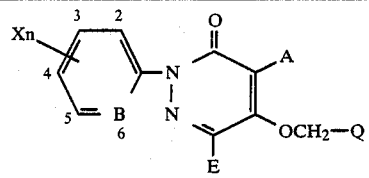

| Compound No. | $X_n$ | Q | E | B | A | m.p. (°C.) |
|---|---|---|---|---|---|---|
| 347 | 4-Cl | Q24 | H | CH | Cl | |
| 348 | 4-Cl | Q24 | H | CH | Br | |
| 349 | 4-Cl | Q25 | H | CH | Cl | |
| 350 | 4-Cl | Q25 | H | CH | Br | |
| 351 | 4-Cl | Q26 | H | CH | Cl | |
| 352 | 4-Cl | Q28 | H | CH | Cl | 187.6~188.1 |
| 353 | 4-Cl | Q27 | H | CH | Cl | 225.0~230.0 |
| 354 | 4-Cl | Q20 | Cl | CH | Cl | |
| 355 | 4-Cl | Q20 | H | N | Cl | |
| 356 | 4-Cl | Q20 | H | CH | H | |
| 357 | 4-Cl | Q29 | H | CH | Br | |
| 358 | 4-Cl | Q30 | H | CH | Br | |
| 359 | 4-Cl | Q31 | H | CH | Br | |
| 360 | 3-Cl | 4-Cl—$C_6H_4$ | H | CH | Br | 171.3~172.0 |
| 361 | 3-Cl | 2,4-$Cl_2$—$C_6H_3$ | H | CH | Br | 155.0~156.0 |
| 362 | 3-Cl | 2-F, 4-Cl—$C_6H_3$ | H | CH | Cl | |
| 363 | 3-Cl | 2-F, 4-Cl—$C_6H_3$ | H | CH | Br | |
| 364 | 4-Br | 4-Cl—$C_6H_4$ | H | CH | Br | |
| 365 | 4-Br | 4-Br—$C_6H_4$ | H | CH | Br | |
| 366 | 4-Br | 2,4-$Cl_2$—$C_6H_3$ | H | CH | Cl | 167.0~168.5 |
| 367 | 4-Br | 2,4-$Cl_2C_6H_3$ | H | CH | Br | |
| 368 | 4-Br | 2-F, 4-Cl—$C_6H_3$ | Cl | CH | Cl | |
| 369 | 4-Br | 4-Cl—$C_6H_4$ | $OCH_3$ | CH | Cl | |
| 370 | 4-Br | 2-F, 4-Cl—$C_6H_3$ | H | CH | Cl | 185.2~185.7 |
| 371 | 4-Br | 2-F, 4-Cl—$C_6H_3$ | H | CH | Br | 168.7~169.9 |
| 372 | 4-Br | 2,4,$Cl_2$—$C_6H_3$ | $OCH_3$ | CH | Cl | |
| 373 | 4-Br | 4-Cl—$C_6H_4$ | H | CH | $OCH_3$ | |
| 374 | 4-Br | 4-I—$C_6H_4$ | H | CH | Br | |
| 375 | 4-Br | Q20 | H | N | Br | |
| 376 | 4-Br | Q20 | H | CH | Br | 194.7~195.4 |
| 377 | 4-Br | Q21 | H | CH | Cl | |
| 378 | 4-Br | Q24 | H | CH | Cl | |
| 379 | 4-Br | Q25 | H | CH | Cl | |
| 380 | 4-Br | 2,6-$F_2$, 4-Cl—$C_6H_2$ | H | CH | Cl | |
| 381 | 4-Br | 2,4,6-$Cl_3$—$C_6H_2$ | H | CH | Br | |
| 382 | 4-Br | 2,4,5-$Cl_3$—$C_6H_2$ | H | CH | Cl | |
| 383 | 4-Br | Q3 | H | CH | Br | |
| 384 | 4-Br | Q6 | H | CH | Cl | |
| 385 | 2-$NO_2$ | 4-Cl—$C_6H_4$ | H | CH | Cl | |
| 386 | 2-$NO_2$ | 2,4-$Cl_2$—$C_6H_3$ | H | CH | Cl | |
| 387 | 3-$NO_2$ | 4-Cl—$C_6H_4$ | H | CH | Br | 197.5~198.5 |
| 388 | 3-$NO_2$ | 4-Br—$C_6H_4$ | H | CH | Br | |
| 389 | 3-$NO_2$ | 2-F, 4-Cl—$C_6H_3$ | H | CH | Cl | |
| 390 | 3-$NO_2$ | 4-Hex—$C_6H_4$ | H | CH | Cl | |
| 391 | 3-$NO_2$ | 4-$CF_3$—$C_6H_4$ | H | CH | Br | |
| 392 | 4-$NO_2$ | 4-Cl—$C_6H_4$ | H | CH | Cl | 214.0~216.0 |
| 393 | 4-$NO_2$ | 4-Cl—$C_6H_4$ | H | CH | Br | 202.0~209.0 |
| 394 | 4-$NO_2$ | 2,4-$Cl_2$—$C_6H_3$ | H | CH | Cl | |
| 395 | 4-$NO_2$ | 2,3-$Cl_2$—$C_6H_3$ | H | CH | Br | 231.0~239.0 |
| 396 | 4-$NO_2$ | 2-F, 4-Cl—$C_6H_3$ | H | CH | Cl | |
| 397 | 4-$NO_2$ | 2-F, 4-Cl—$C_6H_3$ | H | CH | Br | 189.0~190.5 |
| 398 | 4-$NO_2$ | 4-Br—$C_6H_4$ | H | CH | Br | |
| 399 | 4-$NO_2$ | Q20 | H | CH | Cl | |
| 400 | 4-$NO_2$ | Q21 | H | CH | Cl | |
| 401 | 4-$NO_2$ | Q20 | H | CH | Br | 211.0~212.0 |
| 402 | 4-$NO_2$ | Q24 | H | CH | Cl | |
| 403 | 4-$NO_2$ | Q25 | H | CH | Br | |
| 404 | 4-$NO_2$ | Q32 | H | CH | Cl | |
| 405 | 2-$OCH_3$ | 4-Cl—$C_6H_4$ | H | CH | Cl | |
| 406 | 2-$OCH_3$ | 4-Cl—$C_6H_4$ | H | CH | Br | |
| 407 | 3-$OCH_3$ | 4-Cl—$C_6H_4$ | H | CH | Cl | |
| 408 | 3-$OCH_3$ | 4-Br—$C_6H_4$ | H | CH | Br | |
| 409 | 3-$OCH_3$ | 2,4-$Cl_2$—$C_6H_3$ | H | CH | Cl | |
| 410 | 4-$OCH_3$ | 4-Cl—$C_6H_4$ | H | CH | Cl | 165.5~166.1 |
| 411 | 4-$OCH_3$ | 4-Cl—$C_6H_4$ | H | H | Br | |
| 412 | 4-$OCH_3$ | 4-Br—$C_6H_4$ | H | CH | Cl | 223.6~224.5 |
| 413 | 4-$OCH_3$ | 2,4-$Cl_2$—$C_6H_3$ | H | CH | Cl | 217.2~218.2 |
| 414 | 4-$OCH_3$ | 2-F, 4-Cl—$C_6H_3$ | H | CH | Cl | |
| 415 | 4-$OCH_3$ | Q20 | H | CH | Cl | |
| 416 | 4-$OCH_3$ | Q22 | H | CH | Cl | |
| 417 | 4-$OCH_3$ | Q21 | H | CH | Br | |

TABLE 1-b-continued

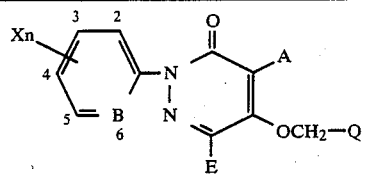

| Compound No. | $X_n$ | Q | E | B | A | m.p. (°C.) |
|---|---|---|---|---|---|---|
| 418 | 4-OCH$_3$ | 4-CF$_3$—C$_6$H$_4$ | H | CH | H | |
| 419 | 4-OCH$_3$ | 4-I—C$_6$H$_4$ | H | CH | Br | |
| 420 | 2-CF$_3$ | 2-F, 4-Cl—C$_6$H$_3$ | H | CH | Br | |
| 421 | 2-CF$_3$ | 2-F, 4-Cl—C$_6$H$_3$ | H | CH | Cl | |
| 422 | 3-CF$_3$ | 4-Cl—C$_6$H$_4$ | H | CH | Br | |
| 423 | 3-CF$_3$ | 4-Br—C$_6$H$_4$ | H | CH | Br | |
| 424 | 3-CF$_3$ | Q20 | H | CH | Br | |
| 425 | 3-CF$_3$ | Q32 | H | CH | Br | |
| 426 | 3-CF$_3$ | Q25 | H | CH | Br | |
| 427 | 3-CF$_3$ | Q22 | H | CH | Br | |
| 428 | 4-CF$_3$ | 2,4-Cl$_2$—C$_6$H$_3$ | H | CH | Br | |
| 429 | 4-CF$_3$ | 2-F, 4-Cl—C$_6$H$_3$ | H | CH | Br | |
| 430 | 4-CF$_3$ | 4-Cl—C$_6$H$_4$ | Cl | CH | Cl | |
| 431 | 4-CF$_3$ | 4-Cl—C$_6$H$_4$ | OPro | CH | Cl | |
| 432 | 4-CF$_3$ | 4-Cl—C$_6$H$_4$ | H | N | Br | |
| 433 | 4-CF$_3$ | 2,4-Cl$_2$C$_6$H$_3$ | H | N | Cl | |
| 434 | 4-CF$_3$ | 4-Cl—C$_6$H$_4$ | H | CH | OEt | |
| 435 | 4-CF$_3$ | 4-Br—C$_6$H$_4$ | H | CH | OBu | |
| 436 | 4-CF$_3$ | 4-Cl—C$_6$H$_4$ | H | CH | OCH$_3$ | |
| 437 | 4-CO$_2$CH$_3$ | 4-Cl—C$_6$H$_4$ | H | CH | Br | |
| 438 | 4-CO$_2$CH$_3$ | 4-Me—C$_6$H$_4$ | H | CH | Br | |
| 439 | 4-CO$_2$CH$_3$ | 4-Br—C$_6$H$_4$ | H | CH | Br | |
| 440 | 4-CO$_2$CH$_3$ | 2,4-Cl$_2$—C$_6$H$_3$ | H | CH | Cl | |
| 441 | 4-CO$_2$CH$_3$ | 2-F, 4-Cl—C$_6$H$_3$ | H | CH | Cl | |
| 442 | 4-CO$_2$Et | 4-Cl—C$_6$H$_4$ | H | CH | Cl | 195.0~196.0 |
| 443 | 4-CO$_2$Et | 4-Cl—C$_6$H$_4$ | H | CH | Br | |
| 444 | 4-CO$_2$Et | 2,4-Cl$_2$—C$_6$H$_3$ | H | CH | Cl | |
| 445 | 4-CO$_2$Et | 2-Me, 4-Cl—C$_6$H$_3$ | H | CH | Br | |
| 446 | 4-CO$_2$Et | 4-Br—C$_6$H$_4$ | H | CH | Cl | |
| 447 | 4-CO$_2$Et | 4-Me—C$_6$H$_4$ | H | CH | Cl | |
| 448 | 4-CO$_2$Et | 2-F, 4-Cl—C$_6$H$_3$ | H | CH | Br | |
| 449 | 4-CO$_2$Et | 2-F, 4-Br—C$_6$H$_3$ | H | CH | Br | |
| 450 | 4-CO$_2$Et | Q20 | H | CH | Cl | |
| 451 | 4-CO$_2$Et | Q20 | H | CH | Br | |
| 452 | 4-CO$_2$Et | Q3 | H | CH | Br | |
| 453 | 4-CO$_2$i-Pro | 4-Cl—C$_6$H$_4$ | H | CH | Cl | |
| 454 | 4-CO$_2$Pro | 4-Cl—C$_6$H$_4$ | H | CH | Cl | |
| 455 | 4-CO$_2$Bu | 4-Cl—C$_6$H$_4$ | H | CH | Cl | |
| 456 | 2,3-Cl$_2$ | 4-Cl—C$_6$H$_4$ | H | CH | Cl | |
| 457 | 2,3-Cl$_2$ | 4-Cl—C$_6$H$_4$ | H | CH | Br | |
| 458 | 2,4-Cl$_2$ | 4-Cl—C$_6$H$_4$ | H | CH | Br | 175.0~176.0 |
| 459 | 2,4-Cl$_2$ | 4-Br—C$_6$H$_4$ | H | CH | Br | |
| 460 | 2,4-Cl$_2$ | 2,4-Cl$_2$C$_6$H$_3$ | H | CH | Br | |
| 461 | 2,4-Cl$_2$ | 2-F, 4-Cl—C$_6$H$_3$ | H | CH | Br | |
| 462 | 2,4-Cl$_2$ | 2-F, 4-Br—C$_6$H$_3$ | H | CH | Cl | |
| 463 | 2,4-Cl$_2$ | 4-Pen—C$_6$H$_4$ | H | CH | Cl | |
| 464 | 2,4-Cl$_2$ | 4-i-Bu—C$_6$H$_4$ | H | CH | Br | |
| 465 | 2,4-Cl$_2$ | Q20 | H | CH | Cl | |
| 466 | 2,4-Cl$_2$ | Q24 | H | CH | Cl | |
| 467 | 2,4-Cl$_2$ | Q21 | H | CH | Br | |
| 468 | 2,4-Cl$_2$ | Q4 | H | CH | Br | |
| 469 | 2,4-Cl$_2$ | Q11 | H | CH | Br | |
| 470 | 2,4-Cl$_2$ | 4-Cl—C$_6$H$_4$ | OCH$_3$ | CH | Cl | |
| 471 | 2,4-Cl$_2$ | 4-Cl—C$_6$H$_4$ | OH | CH | Cl | |
| 472 | 2,4-Cl$_2$ | 4-Cl—C$_6$H$_4$ | Br | CH | Br | |
| 473 | 2,4-Cl$_2$ | 4-Cl—C$_6$H$_4$ | H | N | Cl | |
| 474 | 2,4-Cl$_2$ | 4-Br—C$_6$H$_4$ | H | N | Cl | |
| 475 | 2,4-Cl$_2$ | 2,4-Cl$_2$—C$_6$H$_3$ | H | CH | H | |
| 476 | 2,4-Cl$_2$ | 4-F—C$_6$H$_4$ | H | CH | OCH$_3$ | |
| 477 | 2,4-Cl$_2$ | 4-Br—C$_6$H$_4$ | H | CH | OBu | |
| 478 | 2,4-Cl$_2$ | Q20 | H | N | Cl | |
| 479 | 2,4-Cl$_2$ | Q20 | H | CH | H | |
| 480 | 2,5-Cl$_2$ | 4-Cl—C$_6$H$_4$ | H | CH | Cl | 171.5~172.5 |
| 481 | 2,5-Cl$_2$ | 4-Cl—C$_6$H$_4$ | H | CH | Br | 185.0~186.0 |
| 482 | 2,5-Cl$_2$ | 2,4-Cl$_2$—C$_6$H$_3$ | H | CH | Cl | |
| 483 | 2,5-Cl$_2$ | 4-Br—C$_6$H$_4$ | H | CH | Cl | |
| 484 | 2,5-Cl$_2$ | 4-Et—C$_6$H$_4$ | H | CH | Br | |
| 485 | 2,5-Cl$_2$ | 2-Me, 4-Pro—C$_6$H$_3$ | H | CH | Br | |
| 486 | 2,5-Cl$_2$ | Q21 | H | CH | Cl | |
| 487 | 2,5-Cl$_2$ | Q8 | H | CH | Br | |
| 488 | 2,6-Cl$_2$ | 4-Me—C$_6$H$_4$ | H | CH | Cl | |

TABLE 1-b-continued

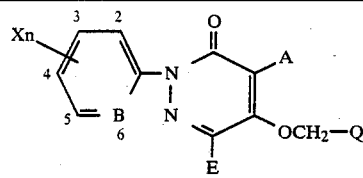

| Compound No. | $X_n$ | Q | E | B | A | m.p. (°C.) |
|---|---|---|---|---|---|---|
| 489 | 2,6-Cl$_2$ | 4-(4-ClC$_6$H$_4$)C$_6$H$_4$ | H | CH | Cl | |
| 490 | 2,6-Cl$_2$ | 4-HexO—C$_6$H$_4$ | H | CH | Cl | |
| 491 | 2,6-Cl$_2$ | 4-(4-ClC$_6$H$_4$CH$_2$)C$_6$H$_4$ | H | CH | Cl | |
| 492 | 3,4-Cl$_2$ | 4-Me—C$_6$H$_4$ | H | CH | Br | 202.0~203.0 |
| 493 | 3,4-Cl$_2$ | 3-Me—C$_6$H$_4$ | H | CH | Cl | |
| 494 | 3,4-Cl$_2$ | 3-Me—C$_6$H$_4$ | H | CH | Br | |
| 495 | 3,4-Cl$_2$ | 2-Me—C$_6$H$_4$ | H | CH | Br | |
| 496 | 3,4-Cl$_2$ | 2-MeO—C$_6$H$_4$ | H | CH | Br | |
| 497 | 3,4-Cl$_2$ | 4-(4-BrC$_6$H$_4$CO)C$_6$H$_4$ | H | CH | Cl | |
| 498 | 3,4-Cl$_2$ | 3-PenO—C$_6$H$_4$ | H | CH | Br | |
| 499 | 3,4-Cl$_2$ | 4-Cl—C$_6$H$_4$ | H | CH | Cl | 178.3~179.4 |
| 500 | 3,4-Cl$_2$ | 4-Cl—C$_6$H$_4$ | H | CH | Br | 178.0~179.0 |
| 501 | 3,4-Cl$_2$ | 2-Cl—C$_6$H$_4$ | H | CH | Cl | 161.7~162.3 |
| 502 | 3,4-Cl$_2$ | Q1 | H | CH | Br | |
| 503 | 3,4-Cl$_2$ | 4-Br—C$_6$H$_4$ | H | CH | Cl | 175.0~176.0 |
| 504 | 3,4-Cl$_2$ | 4-Br—C$_6$H$_4$ | H | CH | Br | |
| 505 | 3,4-Cl$_2$ | 4-F—C$_6$H$_4$ | H | CH | Br | |
| 506 | 3,4-Cl$_2$ | 3-F—C$_6$H$_4$ | H | CH | Br | |
| 507 | 3,4-Cl$_2$ | 2,4-Cl$_2$—C$_6$H$_3$ | H | CH | Cl | 166.0~167.0 |
| 508 | 3,4-Cl$_2$ | 2,4-Cl$_2$—C$_6$H$_3$ | H | CH | Br | 167.0~171.0 |
| 509 | 3,4-Cl$_2$ | Q33 | H | CH | Cl | |
| 510 | 3,4-Cl$_2$ | 4-I—C$_6$H$_4$ | H | CH | Cl | 182.3~183.2 |
| 511 | 3,4-Cl$_2$ | 4-I—C$_6$H$_4$ | H | CH | Br | |
| 512 | 3,4-Cl$_2$ | 4-CF$_3$—C$_6$H$_4$ | H | CH | Cl | |
| 513 | 3,4-Cl$_2$ | 4-CF$_3$—C$_6$H$_4$ | H | CH | Br | |
| 514 | 3,4-Cl$_2$ | 4-CF$_3$CH$_2$O—C$_6$H$_4$ | H | CH | Br | |
| 515 | 3,4-Cl$_2$ | 4-CHF$_2$CF$_2$CH$_2$O—C$_6$H$_4$ | H | CH | Cl | |
| 516 | 3,4-Cl$_2$ | 4-CHF$_2$O—C$_6$H$_4$ | H | CH | Br | |
| 517 | 3,4-Cl$_2$ | 2,4-Br$_2$—C$_6$H$_3$ | H | CH | Cl | |
| 518 | 3,4-Cl$_2$ | 2,4-Br$_2$—C$_6$H$_3$ | H | CH | Br | |
| 519 | 3,4-Cl$_2$ | 2-Cl, 4-Br—C$_6$H$_3$ | H | CH | Cl | |
| 520 | 3,4-Cl$_2$ | 2-Cl, 4-Br—C$_6$H$_3$ | H | CH | Br | |
| 521 | 3,4-Cl$_2$ | 2-F, 4-Cl—C$_6$H$_3$ | H | CH | Cl | 175.2~176.1 |
| 522 | 3,4-Cl$_2$ | 2-F, 4Cl—C$_6$H$_3$ | H | CH | Br | 172.0~173.0 |
| 523 | 3,4-Cl$_2$ | 2-Cl, 4-F—C$_6$H$_3$ | H | CH | Cl | |
| 524 | 3,4-Cl$_2$ | 2-Cl, 4-F—C$_6$H$_3$ | H | CH | Br | |
| 525 | 3,4-Cl$_2$ | 2-F, 4-Br—C$_6$H$_3$ | H | CH | Cl | 186.2~187.4 |
| 526 | 3,4-Cl$_2$ | 2-F, 4-Br—C$_6$H$_3$ | H | CH | Br | 177.0~178.1 |
| 527 | 3,4-Cl$_2$ | 2,6-F$_2$, 4-Cl—C$_6$H$_2$ | H | CH | Cl | |
| 528 | 3,4-Cl$_2$ | 2,6-F$_2$, 4-Cl—C$_6$H$_2$ | H | CH | Br | |
| 529 | 3,4-Cl$_2$ | 2,4-Cl$_2$, 6-F—C$_6$H$_2$ | H | CH | Br | |
| 530 | 3,4-Cl$_2$ | 2,4,5-Cl$_3$—C$_6$H$_2$ | H | CH | Br | |
| 531 | 3,4-Cl$_2$ | 4-CN—C$_6$H$_4$ | H | CH | Cl | |
| 532 | 3,4-Cl$_2$ | 4-Hex—C$_6$H$_4$ | H | CH | Br | |
| 533 | 3,4-Cl$_2$ | Q7 | H | CH | Br | |
| 534 | 3,4-Cl$_2$ | 4-(4-MeC$_6$H$_4$)C$_6$H$_4$ | H | CH | Cl | |
| 535 | 3,4-Cl$_2$ | 4-(4-MeC$_6$H$_4$CH$_2$O)C$_6$H$_4$ | H | CH | Cl | |
| 536 | 3,4-Cl$_2$ | 4-(4-ClC$_6$H$_4$)C$_6$H$_4$ | H | CH | Br | |
| 537 | 3,4-Cl$_2$ | 4-(4-CF$_3$C$_6$H$_4$CH$_2$O)C$_6$H$_4$ | H | CH | Cl | |
| 538 | 3,4-Cl$_2$ | 4-(4-EtOC$_6$H$_4$CH$_2$O)C$_6$H$_4$ | H | CH | Cl | |
| 539 | 3,4-Cl$_2$ | 4-(4-BrC$_6$H$_4$CH$_2$)C$_6$H$_4$ | H | CH | Br | |
| 540 | 3,4-Cl$_2$ | 4-Cl—C$_6$H$_4$ | H | CH | H | |
| 541 | 3,4-Cl$_2$ | 2,4-Cl$_2$—C$_6$H$_3$ | H | CH | OCH$_3$ | |
| 542 | 3,4-Cl$_2$ | 4-Cl—C$_6$H$_4$ | H | CH | O—i-Pro | |
| 543 | 3,4-Cl$_2$ | 4-Cl—C$_6$H$_4$ | Cl | CH | Cl | |
| 544 | 3,4-Cl$_2$ | 2,4-Cl$_2$—C$_6$H$_3$ | Cl | CH | Cl | |
| 545 | 3,4-Cl$_2$ | 4-Cl—C$_6$H$_4$ | OH | CH | Cl | |
| 546 | 3,4-Cl$_2$ | 4-Cl—C$_6$H$_4$ | OCH$_3$ | CH | Cl | |
| 547 | 3,4-Cl$_2$ | 4-Br—C$_6$H$_4$ | OCH$_3$ | CH | Cl | |
| 548 | 3,4-Cl$_2$ | 4-Me—C$_6$H$_4$ | Cl | CH | Cl | |
| 549 | 3,4-Cl$_2$ | 4-EtO—C$_6$H$_4$ | OEt | CH | Cl | |
| 550 | 3,4-Cl$_2$ | 2-F, 4-Cl—C$_6$H$_3$ | Cl | CH | Cl | |
| 551 | 3,4-Cl$_2$ | 2-F, 4-Cl—C$_6$H$_3$ | H | CH | OCH$_3$ | |
| 552 | 3,4-Cl$_2$ | 2-F, 4-Cl—C$_6$H$_3$ | H | CH | H | |
| 553 | 3,4-Cl$_2$ | 2-F, 4-Br—C$_6$H$_3$ | Cl | CH | Cl | |
| 554 | 3,4-Cl$_2$ | 2-F, 4-Br—C$_6$H$_3$ | H | CH | H | |
| 555 | 3,4-Cl$_2$ | 2-Me, 4-Cl—C$_6$H$_3$ | H | CH | Br | |
| 556 | 3,4-Cl$_2$ | 2-Me, 4-Br—C$_6$H$_3$ | H | CH | Cl | |
| 557 | 3,4-Cl$_2$ | 4-Cl—C$_6$H$_4$ | H | CH | O—s-Bu | |
| 558 | 3,4-Cl$_2$ | 4-Br—C$_6$H$_4$ | H | CH | OEt | |
| 559 | 3,4-Cl$_2$ | 4-Br—C$_6$H$_4$ | H | CH | OBu | |

TABLE 1-b-continued

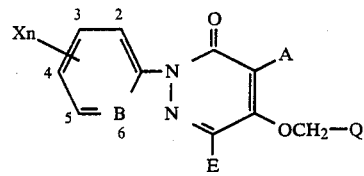

| Compound No. | $X_n$ | Q | E | B | A | m.p. (°C.) |
|---|---|---|---|---|---|---|
| 560 | 3,4-Cl₂ | Q3 | H | CH | Cl | |
| 561 | 3,4-Cl₂ | Q3 | H | CH | Br | |
| 562 | 3,4-Cl₂ | Q4 | H | CH | Br | |
| 563 | 3,4-Cl₂ | Q4 | Cl | CH | Cl | |
| 564 | 3,4-Cl₂ | Q15 | H | CH | Cl | |
| 565 | 3,4-Cl₂ | Q12 | H | CH | Cl | |
| 566 | 3,4-Cl₂ | Q34 | H | CH | Br | |
| 567 | 3,4-Cl₂ | Q5 | H | CH | Br | |
| 568 | 3,4-Cl₂ | Q8 | H | CH | Br | |
| 569 | 3,4-Cl₂ | Q6 | H | CH | Br | |
| 570 | 3,4-Cl₂ | Q6 | H | CH | Cl | 203.3~205.6 |
| 571 | 3,4-Cl₂ | Q10 | H | CH | Br | |
| 572 | 3,4-Cl₂ | Q9 | H | CH | Br | |
| 573 | 3,4-Cl₂ | Q9 | Cl | CH | Cl | |
| 574 | 3,4-Cl₂ | Q11 | H | CH | Br | |
| 575 | 3,4-Cl₂ | Q12 | H | CH | Br | |
| 576 | 3,4-Cl₂ | Q35 | Cl | CH | Cl | |
| 577 | 3,4-Cl₂ | Q13 | H | CH | Cl | |
| 578 | 3,4-Cl₂ | Q14 | H | CH | Br | |
| 579 | 3,4-Cl₂ | Q36 | H | CH | Br | |
| 580 | 3,4-Cl₂ | Q16 | H | CH | Br | |
| 581 | 3,4-Cl₂ | Q18 | H | CH | Br | |
| 582 | 3,4-Cl₂ | Q20 | H | CH | Cl | 173.0~176.0 |
| 583 | 3,4-Cl₂ | Q20 | H | CH | Br | 193.0~194.0 |
| 584 | 3,4-Cl₂ | Q21 | H | CH | Cl | 184.0~185.0 |
| 585 | 3,4-Cl₂ | Q21 | H | CH | Br | |
| 586 | 3,4-Cl₂ | Q22 | H | CH | Cl | 177.5~178.5 |
| 587 | 3,4-Cl₂ | Q22 | H | CH | Br | |
| 588 | 3,4-Cl₂ | Q37 | H | CH | Cl | |
| 589 | 3,4-Cl₂ | Q37 | H | CH | Br | |
| 590 | 3,4-Cl₂ | Q24 | H | CH | Cl | more than 210 |
| 591 | 3,4-Cl₂ | Q24 | H | CH | Br | |
| 592 | 3,4-Cl₂ | Q32 | H | CH | Cl | |
| 593 | 3,4-Cl₂ | Q32 | H | CH | Br | |
| 594 | 3,4-Cl₂ | Q25 | H | CH | Cl | |
| 595 | 3,4-Cl₂ | Q25 | H | CH | Br | |
| 596 | 3,4-Cl₂ | Q23 | H | CH | Cl | |
| 597 | 3,4-Cl₂ | Q38 | H | CH | Cl | |
| 598 | 3,4-Cl₂ | Q39 | H | CH | Br | 184.0~187.0 |
| 599 | 3,4-Cl₂ | Q30 | H | CH | Br | |
| 600 | 3,5-Cl₂ | 4-Cl—C₆H₄ | H | CH | Cl | |
| 601 | 3,5-Cl₂ | 4-Cl—C₆H₄ | H | CH | Br | 187.5~188.1 |
| 602 | 3,5-Cl₂ | 4-Br—C₆H₄ | H | CH | Br | |
| 603 | 3,5-Cl₂ | 2-F, 4-Cl—C₆H₃ | H | CH | Br | 171.1~171.5 |
| 604 | 3,5-Cl₂ | Q20 | H | CH | Br | |
| 605 | 4-Cl, 2-F | 2,4-Cl₂—C₆H₃ | H | CH | Cl | 189.7~190.8 |
| 606 | 4-Cl, 2-F | 2,4-Cl₂—C₆H₃ | H | CH | Br | 183.0~185.0 |
| 607 | 4-Cl, 2-F | 2-F, 4-Cl—C₆H₃ | H | CH | Cl | 175.7~177.2 |
| 608 | 4-Cl, 2-F | 2-F, 4-Cl—C₆H₃ | H | CH | Br | 171.0~172.0 |
| 609 | 4-Cl, 2-F | 4-I—C₆H₄ | H | CH | Cl | 179.9~186.4 |
| 610 | 4-Cl, 2-F | 4-I—C₆H₄ | H | CH | Br | |
| 611 | 4-Cl, 2-F | 2,4-F₂—C₆H₃ | H | CH | Cl | 162.0~162.9 |
| 612 | 4-Cl, 2-F | 2,4-F₂—C₆H₃ | H | CH | Br | 179.6~181.0 |
| 613 | 4-Cl, 2-F | 2-Cl, 4-F—C₆H₃ | H | CH | Br | 163.3~164.1 |
| 614 | 4-Cl, 2-F | 2-F, 4-Br—C₆H₃ | H | CH | Cl | 185.7~187.2 |
| 615 | 4-Cl, 2-F | 2-F, 4-Br—C₆H₃ | H | CH | Br | 177.3~178.6 |
| 616 | 4-Cl, 2-F | 4-Bu—C₆H₄ | H | CH | Cl | |
| 617 | 4-Cl, 2-F | 4-i-BuO—C₆H₄ | H | CH | Cl | |
| 618 | 4-Cl, 2-F | 2,6-F₂, 4-Cl—C₆H₂ | H | CH | Br | |
| 619 | 4-Cl, 2-F | 2,6-F₂, 4-Cl—C₆H₂ | H | CH | Cl | |
| 620 | 4-Cl, 2-F | 2-Me, 4-Cl—C₆H₃ | H | CH | Br | |
| 621 | 4-Cl, 2-F | 2-Me, 4-Br—C₆H₃ | H | CH | Br | |
| 622 | 4-Cl, 2-F | Q12 | H | CH | Cl | |
| 623 | 4-Cl, 2-F | Q12 | H | CH | Br | |
| 624 | 4-Cl, 2-F | 4-Cl—C₆H₄ | OH | CH | Cl | |
| 625 | 4-Cl, 2-F | 4-Cl—C₆H₄ | OCH₃ | CH | Cl | |
| 626 | 4-Cl, 2-F | 4-Br—C₆H₄ | OEt | CH | Cl | |
| 627 | 4-Cl, 2-F | 4-Cl—C₆H₄ | Cl | CH | Cl | |
| 628 | 4-Cl, 2-F | 4-Cl—C₆H₄ | H | CH | H | |
| 629 | 4-Cl, 2-F | 2,4-Cl₂—C₆H₃ | H | CH | H | |
| 630 | 4-Cl, 2-F | 4-Cl—C₆H₄ | H | CH | OCH₃ | |

TABLE 1-b-continued

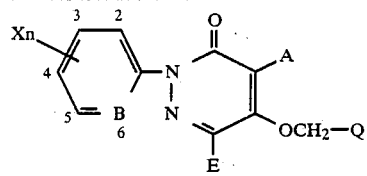

| Compound No. | $X_n$ | Q | E | B | A | m.p. (°C.) |
|---|---|---|---|---|---|---|
| 631 | 4-Cl, 2-F | 2,4-Cl$_2$—C$_6$H$_3$ | H | CH | OCH$_3$ | |
| 632 | 4-Cl, 2-F | 4-Cl—C$_6$H$_4$ | H | CH | OPro | |
| 633 | 4-Cl, 2-F | 2,4-Cl$_2$—C$_6$H$_3$ | H | CH | O—i-Bu | |
| 634 | 4-Cl, 2-F | 4-Me—C$_6$H$_4$ | H | CH | OCH$_3$ | |
| 635 | 4-Cl, 2-F | 4-Cl—C$_6$H$_4$ | H | N | Cl | |
| 636 | 4-Cl, 2-F | 4-Cl—C$_6$H$_4$ | H | N | Br | |
| 637 | 4-Cl, 2-F | 2-F, 4-Cl—C$_6$H$_3$ | H | N | Cl | |
| 638 | 4-Cl, 2-F | Q3 | H | CH | Br | |
| 639 | 4-Cl, 2-F | Q4 | H | CH | Br | 148.0~150.0 |
| 640 | 4-Cl, 2-F | Q4 | H | CH | Cl | |
| 641 | 4-Cl, 2-F | Q15 | H | CH | Br | |
| 642 | 4-Cl, 2-F | Q40 | H | CH | Br | |
| 643 | 4-Cl, 2-F | Q5 | H | CH | Br | |
| 644 | 4-Cl, 2-F | Q8 | H | CH | Br | |
| 645 | 4-Cl, 2-F | Q6 | H | CH | Cl | |
| 646 | 4-Cl, 2-F | Q10 | H | CH | Br | |
| 647 | 4-Cl, 2-F | Q9 | H | CH | Cl | |
| 648 | 4-Cl, 2-F | Q11 | H | CH | Br | |
| 649 | 4-Cl, 2-F | Q35 | H | CH | Br | |
| 650 | 4-Cl, 2-F | Q14 | H | CH | Cl | |
| 651 | 4-Cl, 2-F | Q41 | H | CH | Cl | |
| 652 | 4-Cl, 2-F | Q20 | H | CH | Cl | 157.0~158.0 |
| 653 | 4-Cl, 2-F | Q20 | H | CH | Br | 189.0~191.0 |
| 654 | 4-Cl, 2-F | Q21 | H | CH | Cl | |
| 655 | 4-Cl, 2-F | Q21 | H | CH | Br | |
| 656 | 4-Cl, 2-F | Q22 | H | CH | Br | |
| 657 | 4-Cl, 2-F | Q37 | H | CH | Br | |
| 658 | 4-Cl, 2-F | Q42 | H | CH | Br | |
| 659 | 4-Cl, 2-F | Q18 | H | CH | Br | |
| 660 | 4-Cl, 2-F | Q43 | H | CH | Br | |
| 661 | 4-Cl, 2-F | Q44 | H | CH | Cl | |
| 662 | 4-Cl, 2-F | Q24 | H | CH | Cl | |
| 663 | 4-Cl, 2-F | Q24 | H | CH | Br | |
| 664 | 4-Cl, 2-F | Q32 | H | CH | Br | |
| 665 | 4-Cl, 2-F | Q25 | H | CH | Cl | |
| 666 | 4-Cl, 2-F | Q25 | H | CH | Br | |
| 667 | 4-Cl, 2-F | Q30 | H | CH | Cl | |
| 668 | 4-Cl, 2-F | Q23 | H | CH | Cl | |
| 669 | 4-Cl, 2-F | Q20 | Cl | CH | Cl | |
| 670 | 4-Br, 2-F | 4-I—C$_6$H$_4$ | H | CH | Br | |
| 671 | 4-Br, 2-F | 4-Br—C$_6$H$_4$ | H | CH | Cl | 188.4~189.4 |
| 672 | 4-Br, 2-F | 4-Br—C$_6$H$_4$ | H | CH | Br | 175.0~176.5 |
| 673 | 4-Br, 2-F | 2-F, 4-Cl—C$_6$H$_3$ | H | CH | Cl | 188.2~189.8 |
| 674 | 4-Br, 2-F | 2-F, 4-Cl—C$_6$H$_3$ | H | CH | Br | 190.0~191.5 |
| 675 | 4-Br, 2-F | 2,4-Cl—C$_6$H$_4$ | H | CH | Cl | 212.0~212.6 |
| 676 | 4-Br, 2-F | 2,4-Cl—C$_6$H$_4$ | H | CH | Br | 206.0~207.0 |
| 677 | 4-Br, 2-F | Q20 | H | CH | Cl | 185.0~189.0 |
| 678 | 4-Br, 2-F | Q20 | H | CH | Br | 187.4~188.4 |
| 679 | 4-Br, 2-F | 4-Cl—C$_6$H$_4$ | Cl | CH | Cl | |
| 680 | 4-Cl, 2-CH$_3$ | 4-Cl—C$_6$H$_4$ | H | CH | Cl | 175.0~177.0 |
| 681 | 4-Cl, 2-CH$_3$ | 4-Cl—C$_6$H$_4$ | H | CH | Br | 188.0~189.8 |
| 682 | 4-Cl, 2-CH$_3$ | 2-F, 4-Cl—C$_6$H$_3$ | H | CH | Cl | 187.0~188.5 |
| 683 | 4-Cl, 2-CH$_3$ | 2-F, 4-Cl—C$_6$H$_3$ | H | CH | Br | 199.5~200.6 |
| 684 | 4-Cl, 2-CH$_3$ | Q20 | H | CH | Br | 207.0~208.0 |
| 685 | 4-Br, 2-CH$_3$ | 4-Cl—C$_6$H$_4$ | H | CH | Br | |
| 686 | 4-Br, 2-CH$_3$ | 2,3,4,5,6-F$_5$C$_6$ | H | CH | Br | |
| 687 | 4-Cl, 3-CH$_3$ | 4-Cl—C$_6$H$_4$ | H | CH | Cl | |
| 688 | 4-Cl, 3-CH$_3$ | 4-Cl—C$_6$H$_4$ | H | CH | Br | |
| 689 | 4-Cl, 3-CH$_3$ | 4-C$_6$H$_5$—C$_6$H$_4$ | H | CH | Cl | |
| 690 | 4-Cl, 3-CH$_3$ | 4-BuO—C$_6$H$_4$ | H | CH | Br | |
| 691 | 4-Br, 3-CH$_3$ | 4-Me—C$_6$H$_4$ | H | CH | Cl | |
| 692 | 4-Br, 3-CH$_3$ | 4-CN—C$_6$H$_4$ | H | CH | Br | |
| 693 | 4-Br, 3-CH$_3$ | 4-CF$_3$—C$_6$H$_4$ | H | CH | Br | |
| 694 | 3-Cl, 4-F | 2,4-(Me)$_2$—C$_6$H$_3$ | H | CH | Br | |
| 695 | 3-Cl, 4-F | 3,4-(Me)$_2$—C$_6$H$_3$ | H | CH | Cl | |
| 696 | 3-Cl, 4-F | 4-Cl—C$_6$H$_4$ | H | CH | Br | 152.4~153.2 |
| 697 | 3-Cl, 4-F | 3,4-Cl$_2$—C$_6$H$_3$ | H | CH | Br | |
| 698 | 3-Cl, 4-F | 4-Me—C$_6$H$_4$ | Cl | CH | Cl | |
| 699 | 3-Cl, 4-F | Q6 | H | CH | Br | |
| 700 | 4-Cl, 3-F | 4-Cl—C$_6$H$_4$ | H | CH | Cl | 183.2~184.6 |
| 701 | 4-Cl, 3-F | 4-Cl—C$_6$H$_4$ | H | CH | Br | 175.0~176.0 |

TABLE 1-b-continued

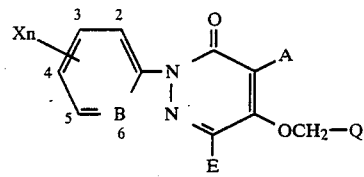

| Compound No. | $X_n$ | Q | E | B | A | m.p. (°C.) |
|---|---|---|---|---|---|---|
| 702 | 4-Cl, 3-F | 2-F, 4-Cl—C$_6$H$_3$ | H | CH | Br | |
| 703 | 4-Br, 3-F | 4-Br—C$_6$H$_4$ | H | CH | Br | |
| 704 | 4-Br, 3-F | 2,4-Cl$_2$—C$_6$H$_3$ | H | CH | Cl | |
| 705 | 4-Br, 3-F | Q20 | H | CH | Br | |
| 706 | 4-Br, 3-Cl | 4-Cl—C$_6$H$_4$ | H | CH | Cl | |
| 707 | 4-Br, 3-Cl | 4-Cl—C$_6$H$_4$ | H | CH | Br | |
| 708 | 4-Br, 3-Cl | 4-Pro—C$_6$H$_4$ | H | CH | Cl | |
| 709 | 4-Br, 3-Cl | Q21 | H | CH | Cl | |
| 710 | 2,4-Br$_2$ | 4-I—C$_6$H$_4$ | H | CH | Cl | |
| 711 | 2,4-Br$_2$ | 2,4-Cl$_2$—C$_6$H$_3$ | H | CH | Br | |
| 712 | 2,4-Br$_2$ | 4-Hex—C$_6$H$_4$ | H | CH | Cl | |
| 713 | 3,4-Br$_2$ | 4-Cl—C$_6$H$_4$ | H | CH | Cl | |
| 714 | 3,4-Br$_2$ | 4-Br—C$_6$H$_4$ | H | CH | Br | |
| 715 | 3,4-Br$_2$ | 4-Me—C$_6$H$_4$ | H | CH | Br | |
| 716 | 3,4-Br$_2$ | 3-Br—C$_6$H$_4$ | H | CH | Cl | |
| 717 | 4-Cl, 3-CF$_3$ | 4-Cl—C$_6$H$_4$ | H | CH | Cl | 155.9~156.8 |
| 718 | 4-Cl, 3-CF$_3$ | 4-Cl—C$_6$H$_4$ | H | CH | Br | 165.0~165.8 |
| 719 | 4-Cl, 3-CF$_3$ | 2-F, 4-Cl—C$_6$H$_3$ | H | CH | Br | 161.7~164.0 |
| 720 | 4-Cl, 3-CF$_3$ | 2-F, 4-Cl—C$_6$H$_3$ | H | CH | Cl | 161.9~163.6 |
| 721 | 4-Cl, 3-CF$_3$ | 2,4-Cl$_2$—C$_6$H$_3$ | H | CH | Cl | 153.5~154.5 |
| 722 | 4-Cl, 3-CF$_3$ | 2-Cl, 4-Br—C$_6$H$_3$ | H | CH | Br | |
| 723 | 4-Cl, 3-CF$_3$ | 2-F, 4-Br—C$_6$H$_3$ | H | CH | Br | |
| 724 | 4-Cl, 3-CF$_3$ | 4-Me—C$_6$H$_4$ | H | CH | Br | |
| 725 | 4-Cl, 3-CF$_3$ | 4-CF$_3$—C$_6$H$_4$ | H | CH | Br | |
| 726 | 4-Cl, 3-CF$_3$ | Q11 | H | CH | Br | |
| 727 | 4-Cl, 3-CF$_3$ | Q20 | H | CH | Cl | 171.0~172.0 |
| 728 | 4-Cl, 3-CF$_3$ | Q21 | H | CH | Br | |
| 729 | 4-Cl, 3-CF$_3$ | Q23 | H | CH | Br | |
| 730 | 2-Cl, 4-CF$_3$ | 2,4-Cl$_2$—C$_6$H$_3$ | H | CH | Br | |
| 731 | 2-Cl, 4-CF$_3$ | 4-Br—C$_6$H$_4$ | H | N | Br | |
| 732 | 2,3,4-Cl$_3$ | 4-Cl—C$_6$H$_4$ | H | CH | Cl | |
| 733 | 2,3,4-Cl$_3$ | 4-Cl—C$_6$H$_4$ | H | CH | Br | |
| 734 | 2,3,4-Cl$_3$ | 2-F, 4-Cl—C$_6$H$_3$ | H | CH | Br | |
| 735 | 2,3,4-Cl$_3$ | 2-F, 4-Cl—C$_6$H$_3$ | H | CH | Cl | |
| 736 | 2,3,4-Cl$_3$ | 2,4-Cl$_2$—C$_6$H$_3$ | H | CH | Cl | |
| 737 | 2,3,4-Cl$_3$ | 4-Br—C$_6$H$_4$ | H | CH | Br | |
| 738 | 2,4,5-Cl$_3$ | 4-Cl—C$_6$H$_4$ | H | CH | Cl | 189.1~191.5 |
| 739 | 2,4,5-Cl$_3$ | 4-Cl—C$_6$H$_4$ | H | CH | Br | 161.0~162.0 |
| 740 | 2,4,5-Cl$_3$ | 4-Br—C$_6$H$_4$ | H | CH | Cl | 202.0~204.0 |
| 741 | 2,4,5-Cl$_3$ | 4-Br—C$_6$H$_4$ | H | CH | Br | 184.2~185.0 |
| 742 | 2,4,5-Cl$_3$ | 2,3-Cl$_2$—C$_6$H$_3$ | H | CH | Cl | 224.8~226.2 |
| 743 | 2,4,5-Cl$_3$ | 2-F, 4-Cl—C$_6$H$_3$ | H | CH | Cl | 195.0~196.0 |
| 744 | 2,4,5-Cl$_3$ | 2-F, 4-Cl—C$_6$H$_3$ | H | CH | Br | 189.5~190.3 |
| 745 | 2,4,5-Cl$_3$ | Q12 | H | CH | Cl | |
| 746 | 2,4,5-Cl$_3$ | Q3 | H | CH | Br | |
| 747 | 4-Cl, 2,6-F$_2$ | 4-Cl—C$_6$H$_4$ | H | CH | Br | |
| 748 | 4-Cl, 2,6-F$_2$ | 4-Me—C$_6$H$_4$ | H | CH | Cl | |
| 749 | 4-Cl, 2,6-F$_2$ | 2-Cl—C$_6$H$_4$ | H | CH | Br | |
| 750 | 3-Cl, 4-F | 4-Cl—C$_6$H$_4$ | H | CH | Cl | 151.0~154.0 |
| 751 | 3-Cl, 4-F | 4-Br—C$_6$H$_4$ | H | CH | Cl | 150.0~153.0 |
| 752 | 3-Cl, 4-F | 4-Br—C$_6$H$_4$ | H | CH | Br | 140.0~143.0 |
| 753 | 3-Cl, 4-F | 2,4-Cl$_2$—C$_6$H$_3$ | H | CH | Cl | 161.1~166.8 |
| 754 | 3-Cl, 4-F | 2,4-Cl$_2$—C$_6$H$_3$ | H | CH | Br | 154.0~156.0 |
| 755 | 3-Cl, 4-F | 2-F, 4-Cl—C$_6$H$_3$ | H | CH | Cl | 154.9~156.4 |
| 756 | 3-Cl, 4-F | 2-F, 4-Cl—C$_6$H$_3$ | H | CH | Br | 147.0~148.5 |
| 757 | 3-Cl, 4-F | 4-I—C$_6$H$_4$ | H | CH | Cl | 145.1~150.0 |
| 758 | 3-Cl, 4-F | 4-I—C$_6$H$_4$ | H | CH | Br | 157.0~159.0 |
| 759 | 4-Br, 2-F | 4-I—C$_6$H$_4$ | H | CH | Cl | |
| 760 | 2,3,4-Cl$_3$ | 4-Br—C$_6$H$_4$ | H | CH | Cl | |
| 761 | 2,3,4-Cl$_3$ | 2,4-Cl$_2$—C$_6$H$_3$ | H | CH | Br | |
| 762 | 2,3,4-Cl$_3$ | 4-I—C$_6$H$_4$ | H | CH | Cl | |
| 763 | 2,3,4-Cl$_3$ | 4-I—C$_6$H$_4$ | H | CH | Br | |
| 764 | 2,4,5-Cl$_3$ | 2,4,Cl$_2$—C$_6$H$_3$ | H | CH | Br | 202.9~203.7 |
| 765 | 2,4,5-Cl$_3$ | 4-I—C$_6$H$_4$ | H | CH | Cl | |
| 766 | 2,4,5-Cl$_3$ | 4-I—C$_6$H$_4$ | H | CH | Br | |
| 767 | 4-Cl | 4-(4-ClC$_6$H$_4$CO)C$_6$H$_4$ | H | CH | Cl | 212.5~248.2 |
| 768 | 2,3,4-Cl$_3$ | Q20 | H | CH | Cl | 223.0~224.0 |
| 769 | 2,3,4-Cl$_3$ | Q20 | H | CH | Br | 229.0~230.0 |
| 770 | 2,4,5-Cl$_3$ | Q20 | H | CH | Cl | 182.0~183.0 |
| 771 | 2,4,5-Cl$_3$ | Q20 | H | CH | Br | 175.2~176.7 |
| 772 | 4-Cl, 2-CH$_3$ | Q20 | H | CH | Cl | 198.0~199.0 |

TABLE 1-b-continued

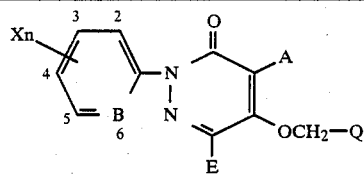

| Compound No. | $X_n$ | Q | E | B | A | m.p. (°C.) |
|---|---|---|---|---|---|---|
| 773 | 4-Cl, 2-CH₃ | Q21 | H | CH | Br | |
| 774 | 4-Cl, 2-CH₃ | 4-Br—C₆H₄ | H | CH | Cl | 184.0~185.0 |
| 775 | 4-Cl, 2-CH₃ | Q24 | H | CH | Cl | |
| 776 | 4-Cl, 2-CF₃ | Q20 | H | CH | Cl | |
| 777 | 4-Cl, 2-CF₃ | Q22 | H | CH | Cl | |
| 778 | 4-Br | Q20 | H | CH | Cl | 202.4~203.4 |
| 779 | 4-Br, 2-F | 2F, 4-Br—C₆H₃ | H | CH | Cl | 188.6~190.4 |
| 780 | 4-Br, 2-F | 2F, 4-Br—C₆H₃ | H | CH | Br | 185.6~186.3 |
| 781 | 4-Cl | 4-Cl—C₆H₄ | H | CH | CH₃ | |
| 782 | 4-Cl | Q20 | H | CH | CH₃ | |
| 783 | 4-Cl | Q24 | H | CH | CH₃ | |
| 784 | 3,4-Cl₂ | 4-Cl—C₆H₄ | H | CH | Et | |
| 785 | 3,4-Cl₂ | Q20 | H | CH | Et | |
| 786 | 3,4,Cl₂ | 4-Cl—C₆H₄ | H | CH | Pro | |
| 787 | 4-Br | 4-Me—C₆H₄ | H | CH | i-Pro | |
| 788 | 4-NO₂ | 4-Br—C₆H₄ | H | CH | i-Pro | |
| 789 | 4-CH₃ | 2,4-Cl₂—C₆H₃ | H | CH | Bu | |
| 790 | 2,4-Cl₂ | Q21 | H | CH | s-Bu | |
| 791 | 4-Cl | Q33 | H | CH | Cl | |
| 792 | 4-Cl | Q33 | H | CH | Br | |
| 793 | 4-Cl | Q36 | H | CH | Cl | |
| 794 | 3,4-Cl₂ | Q33 | H | CH | Br | |
| 795 | 3,4-Cl₂ | Q36 | H | CH | Cl | |
| 796 | 3,4,5-Cl₃ | 4-Cl—C₆H₄ | H | CH | Cl | |
| 797 | 3,4,5-Cl₃ | Q20 | H | CH | Cl | 207.0~211.0 |
| 798 | 3,4,5-Cl₃ | Q20 | H | CH | Br | |
| 799 | 4-Cl, 3-CH₃ | Q20 | H | CH | Cl | |
| 800 | 4-Br, 3-CH₃ | Q20 | H | CH | Cl | |
| 801 | 4-Br, 3-F | Q20 | H | CH | Cl | |
| 802 | 4-Cl, 3-F | Q20 | H | CH | Cl | 176.8~177.8 |
| 803 | 4-Cl, 3-F | Q20 | H | CH | Br | |
| 804 | 4-Br, 3-Cl | Q20 | H | CH | Cl | |
| 805 | 4-Br, 3-Cl | Q20 | H | CH | Br | |
| 806 | 3,4-Br₂ | Q20 | H | CH | Cl | |
| 807 | 3,4-Br₂ | Q20 | H | CH | Br | |
| 808 | 4-Cl, 3-CF₃ | Q20 | H | CH | Br | 177.0~178.0 |
| 809 | 4-Cl, 3-Br | Q20 | H | CH | Cl | 179.4~180.1 |
| 810 | 4-Cl, 3-Br | Q20 | H | CH | Br | |
| 811 | 4-Cl, 3-NO₂ | Q20 | H | CH | Cl | 211.5~223.0 |
| 812 | 4-Cl, 3-NO₂ | Q20 | H | CH | Br | |
| 813 | 4-Cl, 3-OCH₃ | Q20 | H | CH | Cl | |
| 814 | 4-Cl, 3-OCH₃ | Q20 | H | CH | Br | |
| 815 | 4-Cl, 3-Br | 4-Cl—C₆H₄ | H | CH | Cl | 169.5~170.4 |
| 816 | 4-Br, 3-F | 4-Cl—C₆H₄ | H | CH | Cl | |
| 817 | 3,4-Cl₂ | 3,4-Cl₂—C₆H₃ | H | CH | Cl | 180.0~181.0 |
| 818 | 3,4-Cl₂ | 3,4-Cl₂—C₆H₃ | H | CH | Br | 189.0~190.0 |
| 819 | 4-F | 4-Cl—C₆H₄ | H | CH | Cl | |
| 820 | 4-F | 4-Cl—C₆H₄ | H | CH | Br | |
| 821 | 4-F | Q20 | H | CH | Cl | |
| 822 | 4-F | Q20 | H | CH | Br | |
| 823 | 3-Br, 4-F | 4-Cl—C₆H₄ | H | CH | Cl | |
| 824 | 3-Br, 4-F | 4-Cl—C₆H₄ | H | CH | Br | |
| 825 | 3-Br, 4-F | Q20 | H | CH | Cl | |
| 826 | 3-Br, 4-F | Q20 | H | CH | Br | |
| 827 | 4-Cl | Q45 | H | CH | Cl | 206.0~207.0 |
| 828 | 3,4-Cl₂ | Q45 | H | CH | Cl | 195.0~196.0 |
| 829 | 3,4-Cl₂ | Q45 | H | CH | Br | 192.0~193.0 |
| 830 | 4-Cl | 4-Cl—C₆H₄ | H | CH | I | 182.7~183.5 |
| 831 | 4-Cl | Q20 | H | CH | I | 194.9~195.5 |
| 832 | 4-Cl | Q21 | H | CH | I | |
| 833 | 4-Cl | Q45 | H | CH | I | |
| 834 | 3,4-Cl₂ | Q20 | H | CH | I | 195.5~196.0 |
| 835 | 3,4-Cl₂ | 4-Cl—C₆H₄ | H | CH | I | 160.0~161.8 |
| 836 | 3,4-Cl₂ | Q21 | H | CH | I | |
| 837 | 3,4-Cl₂ | Q45 | H | CH | I | 182.0~183.0 |
| 838 | 4-Cl | 2,4-Cl₂—C₆H₃ | H | CH | I | |
| 839 | 3,4-Cl₂ | 2,4-Cl₂—C₆H₃ | H | CH | I | 163.7~164.5 |
| 840 | 4-Cl | Q20 | H | CH | F | |
| 841 | 4-Cl | Q21 | H | CH | F | |
| 842 | 4-Cl | Q45 | H | CH | F | |
| 843 | 4-Cl | 4-Cl—C₆H₄ | H | CH | F | |

TABLE 1-b-continued

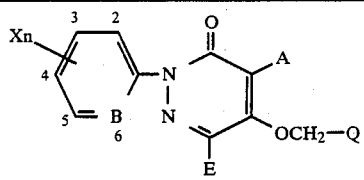

| Compound No. | $X_n$ | Q | E | B | A | m.p. (°C.) |
|---|---|---|---|---|---|---|
| 844 | 4-Cl | 2,4-Cl$_2$—C$_6$H$_3$ | H | CH | F | |
| 845 | 3,4-Cl$_2$ | Q20 | H | CH | F | |
| 846 | 3,4-Cl$_2$ | Q21 | H | CH | F | |
| 847 | 3,4-Cl$_2$ | Q45 | H | CH | F | |
| 848 | 3,4-Cl$_2$ | 4-Cl—C$_6$H$_4$ | H | CH | F | |
| 849 | 3,4-Cl$_2$ | 2,4-Cl$_2$—C$_6$H$_3$ | H | CH | F | |
| 850 | 4-Cl | Q24 | H | CH | I | |
| 851 | 3,4-Cl$_2$ | Q24 | H | CH | I | |
| 852 | 4-Cl | Q12 | H | CH | I | |
| 853 | 3,4-Cl$_2$ | Q12 | H | CH | I | |
| 854 | 4-OCF$_3$ | Q20 | H | CH | Cl | |
| 855 | 4-OCF$_3$ | Q45 | H | CH | Cl | |
| 856 | 4-OCF$_3$ | Q20 | H | CH | I | |
| 857 | 3-Cl, 4-I | 4-Cl—C$_6$H$_4$ | H | CH | Cl | 161.7~163.2 |
| 858 | 3-Cl, 4-I | Q20 | H | CH | Cl | 167.0~169.0 |
| 859 | 3-Cl, 4-I | Q45 | H | CH | Cl | |
| 860 | 3-Cl, 4-I | Q20 | H | CH | Br | |

Q1 to Q45 shown in the above-mentioned Tables are groups represented by the following formulae.

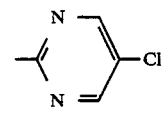 Q1

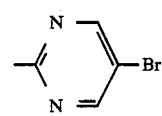 Q2

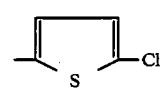 Q3

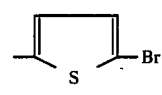 Q4

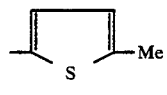 Q5

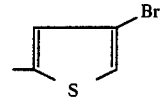 Q6

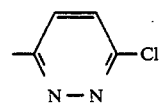 Q7

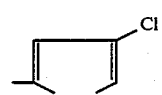 Q8

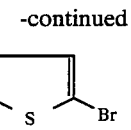 Q9

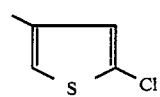 Q10

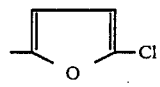 Q11

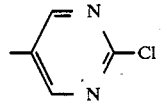 Q12

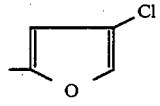 Q13

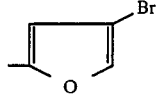 Q14

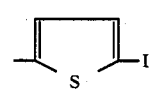 Q15

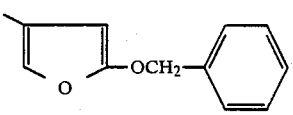 Q16

-continued
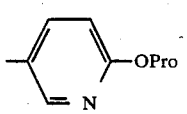 Q17
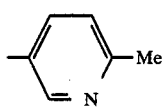 Q18
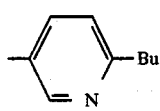 Q19
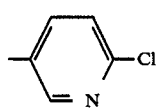 Q20
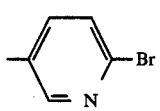 Q21
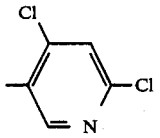 Q22
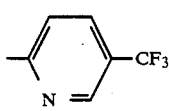 Q23
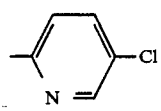 Q24
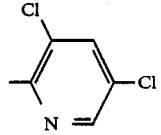 Q25
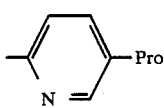 Q26
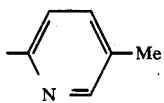 Q27
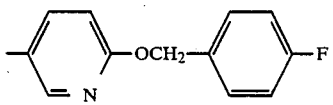 Q28
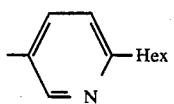 Q29
-continued
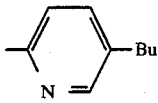 Q30
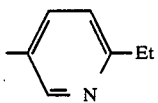 Q31
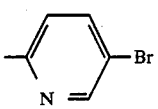 Q32
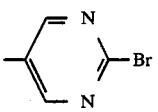 Q33
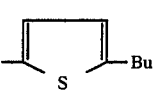 Q34
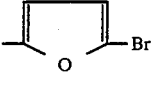 Q35
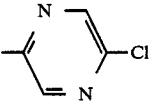 Q36
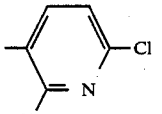 Q37
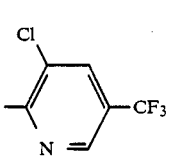 Q38
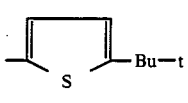 Q39
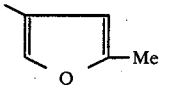 Q40
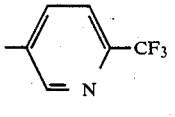 Q41
Q42

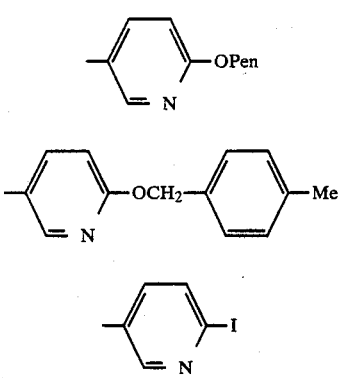

Q43, Q44, Q45

TABLE 2

| Compound No. | Mortality of Green rice leaf-hopper (Nephotettix cincticeps) (%) | Compound No. | Mortality of Green rice leaf-hopper (Nephotettix cincticep) (%) |
|---|---|---|---|
| 12 | 100 | 256 | 100 |
| 22 | 100 | 273 | 100 |
| 27 | 100 | 274 | 100 |
| 28 | 100 | 286 | 100 |
| 33 | 100 | 340 | 100 |
| 34 | 100 | 341 | 100 |
| 35 | 100 | 342 | 100 |
| 49 | 100 | 360 | 100 |
| 51 | 100 | 361 | 100 |
| 97 | 100 | 370 | 100 |
| 154 | 100 | 371 | 100 |
| 166 | 100 | 376 | 100 |
| 167 | 100 | 393 | 100 |
| 170 | 100 | 397 | 100 |
| 171 | 100 | 401 | 100 |
| 172 | 100 | 412 | 100 |
| 174 | 100 | 458 | 100 |
| 175 | 100 | 480 | 100 |
| 178 | 100 | 481 | 100 |
| 189 | 100 | 499 | 100 |
| 190 | 100 | 500 | 100 |
| 235 | 100 | 503 | 100 |
| 507 | 100 | 684 | 100 |
| 508 | 100 | 696 | 100 |
| 510 | 100 | 738 | 100 |
| 521 | 100 | 739 | 100 |
| 522 | 100 | 740 | 100 |
| 582 | 100 | 741 | 100 |
| 583 | 100 | 750 | 100 |
| 584 | 100 | 751 | 100 |
| 590 | 100 | | |
| 605 | 100 | 752 | 100 |
| 606 | 100 | 755 | 100 |
| 607 | 100 | 756 | 100 |
| 608 | 100 | 757 | 100 |
| 609 | 100 | 758 | 100 |
| 639 | 100 | 770 | 100 |
| 652 | 100 | 771 | 100 |
| 653 | 100 | 778 | 100 |
| 671 | 100 | 809 | 100 |
| 672 | 100 | 827 | 100 |
| 673 | 100 | 828 | 100 |
| 674 | 100 | 829 | 100 |
| 675 | 100 | 830 | 100 |
| 676 | 100 | 831 | 100 |
| 677 | 100 | 834 | 100 |
| 678 | 100 | 835 | 100 |
| | | 837 | 100 |
| | | 839 | 100 |
| | | 857 | 100 |
| | | 858 | 100 |
| | | known compound A | 0 |

TABLE 3

| Compound No. | Mortality of Brown rice planthopper (Nilaparvata lugens) (%) | Compound No. | Mortality of Brown rice planthopper (Nilaparvata lugens) (%) |
|---|---|---|---|
| 4 | 100 | 397 | 100 |
| 28 | 100 | 401 | 100 |
| 34 | 100 | 412 | 100 |
| 39 | 100 | 442 | 100 |
| 79 | 100 | 481 | 100 |
| 81 | 100 | 500 | 100 |
| 82 | 100 | 507 | 100 |
| 84 | 100 | 508 | 100 |
| 88 | 100 | 521 | 100 |
| 109 | 100 | 522 | 100 |
| 167 | 100 | 582 | 100 |
| 171 | 100 | 583 | 100 |
| 256 | 100 | 584 | 100 |
| 272 | 100 | 605 | 100 |
| 273 | 100 | 606 | 100 |
| 274 | 100 | 607 | 100 |
| 340 | 100 | 608 | 100 |
| 341 | 100 | 609 | 100 |
| 342 | 100 | 611 | 100 |
| 361 | 100 | 613 | 100 |
| 366 | 100 | 652 | 100 |
| 370 | 100 | 653 | 100 |
| 371 | 100 | 672 | 100 |
| 376 | 100 | 674 | 100 |
| 675 | 100 | 809 | 100 |
| 676 | 100 | 827 | 100 |
| 677 | 100 | 828 | 100 |
| 678 | 100 | 829 | 100 |
| 684 | 100 | 830 | 100 |
| 739 | 100 | 831 | 100 |
| 770 | 100 | 834 | 100 |
| 778 | 100 | 835 | 100 |
| | | 837 | 100 |
| | | 839 | 100 |
| | | 858 | 100 |
| known compound A | | | 0 |

TABLE 4

| Compound No. | Mortality (%) |
|---|---|
| 22 | 0 |
| 27 | 0 |
| 28 | 0 |
| 29 | 0 |
| 36 | 0 |
| 38 | 0 |
| 39 | 0 |
| 49 | 0 |
| 82 | 0 |
| 89 | 0 |
| 109 | 0 |
| 170 | 0 |
| 175 | 0 |
| 342 | 0 |
| 366 | 0 |
| 584 | 0 |
| 809 | 0 |
| 827 | 0 |
| 828 | 0 |
| 829 | 0 |
| 830 | 0 |
| 831 | 0 |
| 834 | 0 |
| 835 | 0 |

TABLE 5

| Compound No. | Mortality (%) |
|---|---|
| 27 | 0 |
| 33 | 0 |
| 97 | 0 |
| 170 | 0 |
| 172 | 0 |
| 342 | 0 |

TABLE 5-continued
| Compound No. | Mortality (%) |
| --- | --- |
| 584 | 0 |
| 809 | 0 |
| 827 | 0 |
| 828 | 0 |
| 829 | 0 |
| 830 | 0 |
| 831 | 0 |
| 834 | 0 |
| 835 | 0 |
TABLE 6
| Compound No. | Chemical Formula |
| --- | --- |
| 27 | 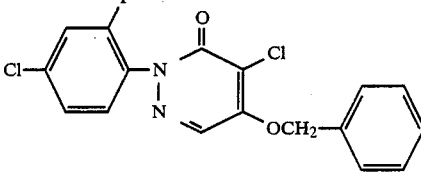 |
| 28 | 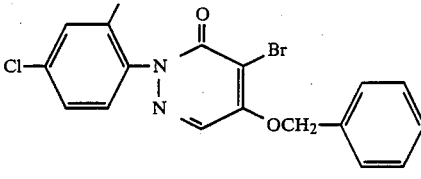 |
| 33 | 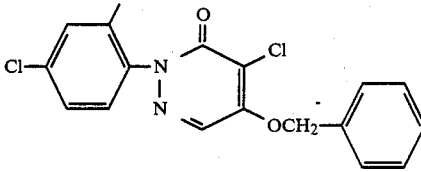 |
| 34 | 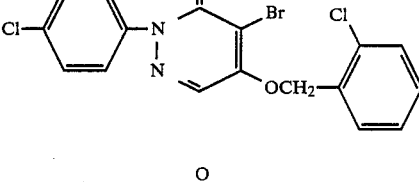 |
| 35 | 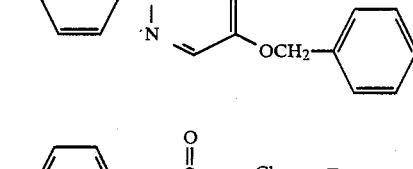 |
| 39 | 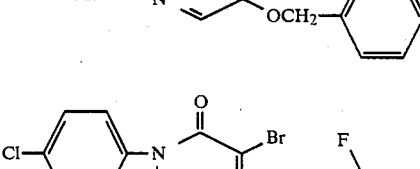 |
| 97 | 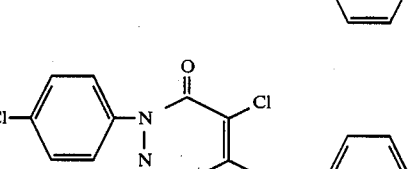 |
| 170 |  |
| 171 |  |
| 172 |  |
| 256 |  |
| 272 |  |
| 273 |  |
| 274 | 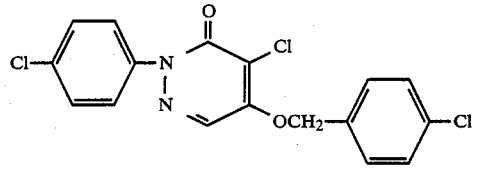 |
| 340 | 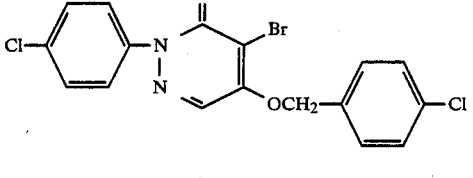 |

TABLE 6-continued

| Compound No. | Chemical Formula |
|---|---|
| 341 | 2-(4-chlorophenyl)-4-bromo-5-[(6-chloropyridin-3-yl)methoxy]pyridazin-3(2H)-one |
| 360 | 2-(3-chlorophenyl)-4-bromo-5-[(4-chlorophenyl)methoxy]pyridazin-3(2H)-one |
| 366 | 2-(4-bromophenyl)-4-chloro-5-[(2,4-dichlorophenyl)methoxy]pyridazin-3(2H)-one |
| 371 | 2-(4-bromophenyl)-4-bromo-5-[(4-chloro-2-fluorophenyl)methoxy]pyridazin-3(2H)-one |
| 376 | 2-(4-chlorophenyl)-4-bromo-5-[(6-chloropyridin-3-yl)methoxy]pyridazin-3(2H)-one |
| 393 | 2-(4-nitrophenyl)-4-bromo-5-[(4-chlorophenyl)methoxy]pyridazin-3(2H)-one |
| 397 | 2-(4-nitrophenyl)-4-bromo-5-[(4-chloro-2-fluorophenyl)methoxy]pyridazin-3(2H)-one |
| 401 | 2-(4-nitrophenyl)-4-bromo-5-[(6-chloropyridin-3-yl)methoxy]pyridazin-3(2H)-one |
| 458 | 2-(2,4-dichlorophenyl)-4-bromo-5-[(4-chlorophenyl)methoxy]pyridazin-3(2H)-one |
| 499 | 2-(3,4-dichlorophenyl)-4-chloro-5-[(4-chlorophenyl)methoxy]pyridazin-3(2H)-one |
| 500 | 2-(3,4-dichlorophenyl)-4-bromo-5-[(4-chlorophenyl)methoxy]pyridazin-3(2H)-one |
| 503 | 2-(3,4-dichlorophenyl)-4-chloro-5-[(4-bromophenyl)methoxy]pyridazin-3(2H)-one |
| 507 | 2-(3,4-dichlorophenyl)-4-chloro-5-[(2,4-dichlorophenyl)methoxy]pyridazin-3(2H)-one |
| 508 | 2-(3,4-dichlorophenyl)-4-bromo-5-[(2,4-dichlorophenyl)methoxy]pyridazin-3(2H)-one |
| 510 | 2-(3,4-dichlorophenyl)-4-chloro-5-[(4-iodophenyl)methoxy]pyridazin-3(2H)-one |

TABLE 6-continued

| Compound No. | Chemical Formula |
|---|---|
| 521 | 3,4-dichlorophenyl-N-N=CH-C(Cl)=C(OCH₂-2-F,4-Cl-phenyl)-C(=O) |
| 522 | 3,4-dichlorophenyl-N-N=CH-C(Br)=C(OCH₂-2-F,4-Cl-phenyl)-C(=O) |
| 582 | 3,4-dichlorophenyl-N-N=CH-C(Cl)=C(OCH₂-6-Cl-pyridin-3-yl)-C(=O) |
| 583 | 3,4-dichlorophenyl-N-N=CH-C(Br)=C(OCH₂-6-Cl-pyridin-3-yl)-C(=O) |
| 605 | 4-Cl,2-F-phenyl-N-N=CH-C(Cl)=C(OCH₂-2,4-dichlorophenyl)-C(=O) |
| 606 | 4-Cl,2-F-phenyl-N-N=CH-C(Br)=C(OCH₂-2,4-dichlorophenyl)-C(=O) |
| 607 | 4-Cl,2-F-phenyl-N-N=CH-C(Cl)=C(OCH₂-2-F,4-Cl-phenyl)-C(=O) |
| 608 | 4-Cl,2-F-phenyl-N-N=CH-C(Br)=C(OCH₂-2-F,4-Cl-phenyl)-C(=O) |
| 609 | 4-Cl,2-F-phenyl-N-N=CH-C(Cl)=C(OCH₂-4-I-phenyl)-C(=O) |
| 613 | 4-Cl,2-F-phenyl-N-N=CH-C(Br)=C(OCH₂-2-Cl,4-F-phenyl)-C(=O) |
| 652 | 4-Cl,2-F-phenyl-N-N=CH-C(Cl)=C(OCH₂-6-Cl-pyridin-3-yl)-C(=O) |
| 653 | 4-Cl,2-F-phenyl-N-N=CH-C(Cl)=C(OCH₂-6-Cl-pyridin-3-yl)-C(=O) |
| 696 | 3-Cl,4-F-phenyl-N-N=CH-C(Br)=C(OCH₂-4-Cl-phenyl)-C(=O) |
| 750 | 3-Cl,4-F-phenyl-N-N=CH-C(Cl)=C(OCH₂-4-Cl-phenyl)-C(=O) |

TABLE 6-continued

| Compound No. | Chemical Formula |
|---|---|
| 751 | 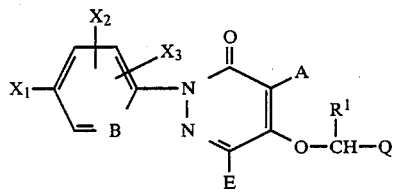 |
| 752 | |
| 757 | |
| 758 | |
| 778 | |

What is claimed is:

1. A compound of the formula:

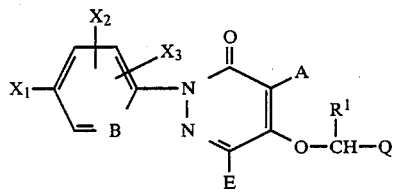

wherein,
$X_1$ represents a halogen, an alkyl having 1 to 4 carbon atoms, nitro, an alkoxy having 1 to 4 carbon atoms or COOR in which R represents an alkyl having 1 to 4 carbon atoms,
$X_2$ represents a hydrogen, a halogen, an alkyl having 1 to 4 carbon atoms or nitro,
$X_3$ represents a hydrogen or a halogen,
A represents a hydrogen, a halogen or an alkoxy having 1 to 4 carbon atoms,
B represents CH or nitrogen,
$R^1$ represents a hydrogen or an alkyl having 1 to 4 carbon atoms,
E represents a hydrogen or an alkoxy having 1 to 4 carbon atoms,
Q represents

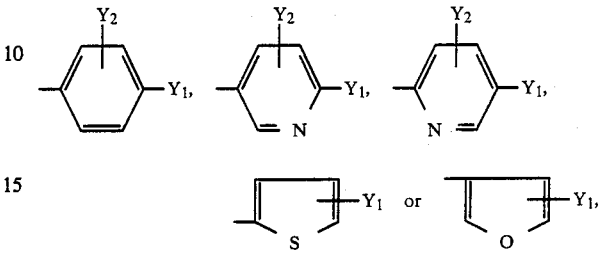

$Y_1$ represents a halogen, an alkyl having 1 to 4 carbon atoms, an alkoxy having 1 to 4 carbon atoms, a haloalkyl having 1 to 4 carbon atoms, a haloalkoxy having 1 to 4 carbon atoms, phenyl group, cyano group, benzyl group or benzoyl group, and $Y_2$ represents a hydrogen, a halogen or an alkyl having 1 to 4 carbon atoms.

2. A compound of the formula:

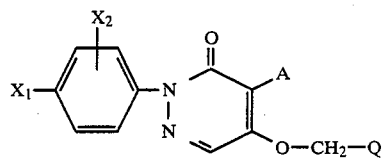

wherein
$X_1$ represents a halogen or nitro,
$X_2$ represents a hydrogen, a halogen, an alkyl having 1 to 4 carbon atoms or nitro,
A represents halogen,
Q represents

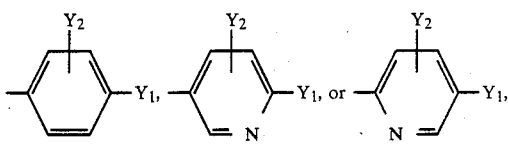

$Y_1$ represents a halogen, an alkyl having 1 to 4 carbon atoms, an alkoxy having 1 to 4 carbon atoms, a haloalkyl having 1 to 4 carbon atoms or a haloalkoxy having 1 to 4 carbon atoms, and
$Y_2$ represents a hydrogen or a halogen.

3. The compound of claim 1, wherein the compound is represented by the formula:

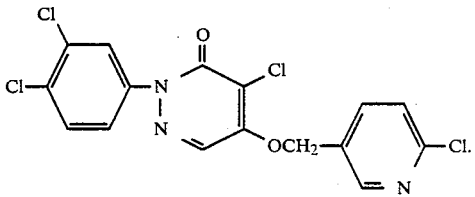

4. The compound of claim 1, wherein the compound is represented by the formula:

5. The compound of claim 1, wherein the compound is represented by the formula:
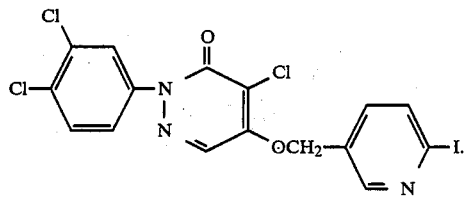
6. The compound of claim 1, wherein the compound is represented by the formula:
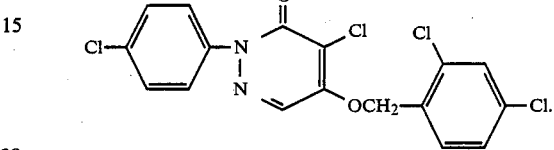
7. An insecticidal composition containing as an active ingredient an effective amount of at least one of the 3(2H)-pyridazinone derivatives of claim 1 together with a suitable carrier and auxiliary agent thereof.
* * * * *